(12) United States Patent
Neumann

(10) Patent No.: US 12,198,808 B2
(45) Date of Patent: Jan. 14, 2025

(54) SYSTEMS AND METHODS FOR SELECTING A TREATMENT SCHEMA BASED ON USER WILLINGNESS

(71) Applicant: KPN INNOVATIONS, LLC, Colorado, CO (US)

(72) Inventor: Kenneth Neumann, Lakewood, CO (US)

( * ) Notice: Subject to any disclaimer, the term of this patent is extended or adjusted under 35 U.S.C. 154(b) by 0 days.

(21) Appl. No.: 16/589,031

(22) Filed: Sep. 30, 2019

(65) Prior Publication Data
US 2021/0098099 A1 Apr. 1, 2021

(51) Int. Cl.
| | |
|---|---|
| G16H 50/20 | (2018.01) |
| G06F 18/2113 | (2023.01) |
| G06F 18/214 | (2023.01) |
| G06F 18/2413 | (2023.01) |
| G06N 20/00 | (2019.01) |
| G06V 10/774 | (2022.01) |
| G06V 10/776 | (2022.01) |
| G06V 10/82 | (2022.01) |
| G16H 20/00 | (2018.01) |

(52) U.S. Cl.
CPC .......... *G16H 50/20* (2018.01); *G06F 18/2113* (2023.01); *G06F 18/214* (2023.01); *G06F 18/24147* (2023.01); *G06N 20/00* (2019.01); *G06V 10/7753* (2022.01); *G06V 10/776* (2022.01); *G06V 10/82* (2022.01); *G16H 20/00* (2018.01)

(58) Field of Classification Search
CPC ...... G16H 20/00; G06N 20/00; G06K 9/6276; G06K 9/623; G06K 9/6256
See application file for complete search history.

(56) References Cited

U.S. PATENT DOCUMENTS

| | | |
|---|---|---|
| 8,655,817 B2 | 2/2014 | Hasey et al. |
| 9,983,670 B2 | 5/2018 | Coleman et al. |
| 10,325,070 B2 | 6/2019 | Beale et al. |
| (Continued) | | |

FOREIGN PATENT DOCUMENTS

WO 2019035125 2/2019

OTHER PUBLICATIONS

Topol, Eric J.; High-Performance Medicine: the Convergence of Human and Artificial Intelligence; Nature Medicine; Jan. 2019.

*Primary Examiner* — Chad A Newton
(74) *Attorney, Agent, or Firm* — Caldwell Intellectual Property Law

(57) ABSTRACT

A system for selecting a treatment schema based on user willingness includes at least a first computing device configured to receive at least a user constitutional datum and at least a user ailment state from at least a second computing device. At least a first computing device is configured to determine, with an adaptive machine learning module, at least a remedial process label. At least a first computing device is configured to derive a remedial attribute list, wherein the remedial attribute list further comprises a plurality of remedial attribute list entries. At least a first computing device is configured to generate a plurality of treatment schemas. At least a first computing device is configured to select a treatment schema from the plurality of treatment schemas. At least a first computing device is configured to transmit the selected treatment schema to at least a second computing device.

19 Claims, 6 Drawing Sheets

(56) References Cited

U.S. PATENT DOCUMENTS

| | | | |
|---|---|---|---|
| 2008/0109252 A1* | 5/2008 | LaFountain | G06Q 50/22 |
| | | | 705/2 |
| 2009/0318775 A1 | 12/2009 | Michelson et al. | |
| 2010/0042438 A1 | 2/2010 | Moore et al. | |
| 2012/0047105 A1* | 2/2012 | Saigal | G16Z 99/00 |
| | | | 706/52 |
| 2014/0122381 A1* | 5/2014 | Nowozin | G06N 20/00 |
| | | | 706/12 |
| 2014/0278448 A1* | 9/2014 | Sadeghi | G06Q 10/10 |
| | | | 705/2 |
| 2017/0011169 A1* | 1/2017 | Chen | G06F 16/24578 |
| 2017/0177822 A1* | 6/2017 | Fogel | G16H 50/20 |
| 2017/0199189 A1 | 7/2017 | Wade | |
| 2017/0228517 A1 | 8/2017 | Saliman et al. | |
| 2017/0235885 A1* | 8/2017 | Cox | G06F 17/277 |
| | | | 705/2 |
| 2018/0166174 A1 | 6/2018 | Lewis | |
| 2018/0241564 A1* | 8/2018 | Peterson | H04W 12/0013 |
| 2019/0096526 A1* | 3/2019 | Hirsch | G06F 21/6245 |
| 2019/0122769 A1 | 4/2019 | Wright et al. | |

\* cited by examiner

SYSTEMS AND METHODS FOR SELECTING A TREATMENT SCHEMA BASED ON USER WILLINGNESS

FIELD OF THE INVENTION

The present invention generally relates to the field of artificial intelligence. In particular, the present invention is directed to systems and methods for selecting a treatment schema based on user willingness.

BACKGROUND

Current treatment plans for remedying ailments are often dismissive of the lifestyle and preferences of the individual being treated. Further, an individual is rarely presented with any degree of choice when it comes to selecting a treatment plan. Lack of choice is compounded by the limited implementation of machine learning processes for developing treatment plans by professionals who are responsible for the diagnosis and treatment of such ailments.

SUMMARY OF THE DISCLOSURE

In an aspect, a system for selecting a treatment schema based on user willingness includes at least a first computing device. The at least a first computing device is designed and configured to receive at least a user constitutional datum from at least a second computing device indicating at least a diagnostic measurement. The at least a first computing device is designed and configured to receive at least a user ailment state from at least a second computing device indicating a current or future ailment. The at least a first computing device is designed and configured to determine, using an adaptive machine learning module, at least a remedial process label using the at least a user constitutional datum and the at least a user ailment state. The at least a first computing device is designed and configured to derive a remedial attribute list from at least a using willingness datum, wherein the remedial attribute list further includes a plurality of remedial attribute list entries including a remedial process label value indicating a degree of importance of at least a remedial process label, and at least a user willingness level value indicating a numerical measure of a user willingness. The at least a first computing device is designed and configured to generate a plurality of treatment schemas, wherein each treatment schema of the plurality of treatment schemas includes a treatment schema attribute listing having a plurality of treatment schema attribute listing entries, the plurality of treatment schema attribute listing entries includes an attribute listing entry corresponding to each remedial attribute list entry of the plurality of remedial attribute list entries, and each treatment schema attribute listing entry indicates a degree of impact on a factor represented by a remedial attribute list entry. The at least a first computing device is designed and configured to select a treatment schema from the plurality of treatment schemas, wherein selecting the treatment schema further includes generating a loss function of the plurality of treatment schemas and the remedial attribute list, minimizing the loss function, and selecting the treatment schema from the plurality of treatment schemas as a function of minimizing the loss function. The at least a first computing device is designed and configured to transmit the selected treatment schema to at least a second computing device.

In another aspect, a method of selecting a treatment schema based on user willingness by at least a first computing device, the method includes receiving at least a user constitutional datum from at least a second computing device indicating at least a diagnostic measurement, receiving at least a user ailment state from at least a second computing device indicating a current or future ailment, determining, with an adaptive machine learning module operating on the at least a first computing device, at least a remedial process label using the at least a user constitutional datum and the at least a user ailment state, deriving a remedial attribute list from at least a user willingness datum, wherein the remedial attribute list further includes a plurality of remedial attribute list entries including a remedial process label value indicating a degree of importance of at least a remedial process label and at least a user willingness level value indicating a numerical measure of a user willingness, generating a plurality of treatment schemas, wherein each treatment schema of the plurality of treatment schemas includes a treatment schema attribute listing having a plurality of treatment schema attribute listing entries, the plurality of treatment schema attribute listing entries includes an attribute listing entry corresponding to each remedial attribute list entry of the plurality of remedial attribute list entries, and each treatment schema attribute listing entry indicates a degree of impact on a factor represented by a remedial attribute list entry, selecting a treatment schema from the plurality of treatment schemas, wherein selecting the treatment schema further includes generating a loss function of the plurality of treatment schemas and the remedial attribute list, minimizing the loss function, selecting the treatment schema from the plurality of treatment schemas as a function of minimizing the loss function, and transmitting the selected treatment schema to the at least a second computing device.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Embodiments disclosed herein use at least a computing device and a combination of machine learning processes to determine a treatment schema of a person diagnosed with an ailment based on physically extracted samples while considering an individual's restrictions and preferences for such a treatment schema. An attribute listing weighting various objectives as derived by further processes is used to match one or more potential treatment schemas for better overcoming an ailment by minimizing a loss functions to find a best-match solution. Classification of data to specific ailments and to willingness of users for treatment schemas may be used to limit training data to closely matched collections.

The terms "computer", "processor", "computer processor", "computing device" or the like should be expansively construed to cover any kind of electronic device with data processing capabilities including, by way of non-limiting example, a digital signal processor (DSP) and/or system on a chip (SoC), a microcontroller, a field programmable gate array (FPGA), an application specific integrated circuit (ASIC), any other kind of electronic device as described in this disclosure, and/or any other electronic computing device including one or more processors of any kind, or any combination thereof. As used herein, the phrase "for example," "such as," "for instance," "in an embodiment," and variants thereof describe non-limiting embodiments of the presently disclosed subject matter.

Figure 1:
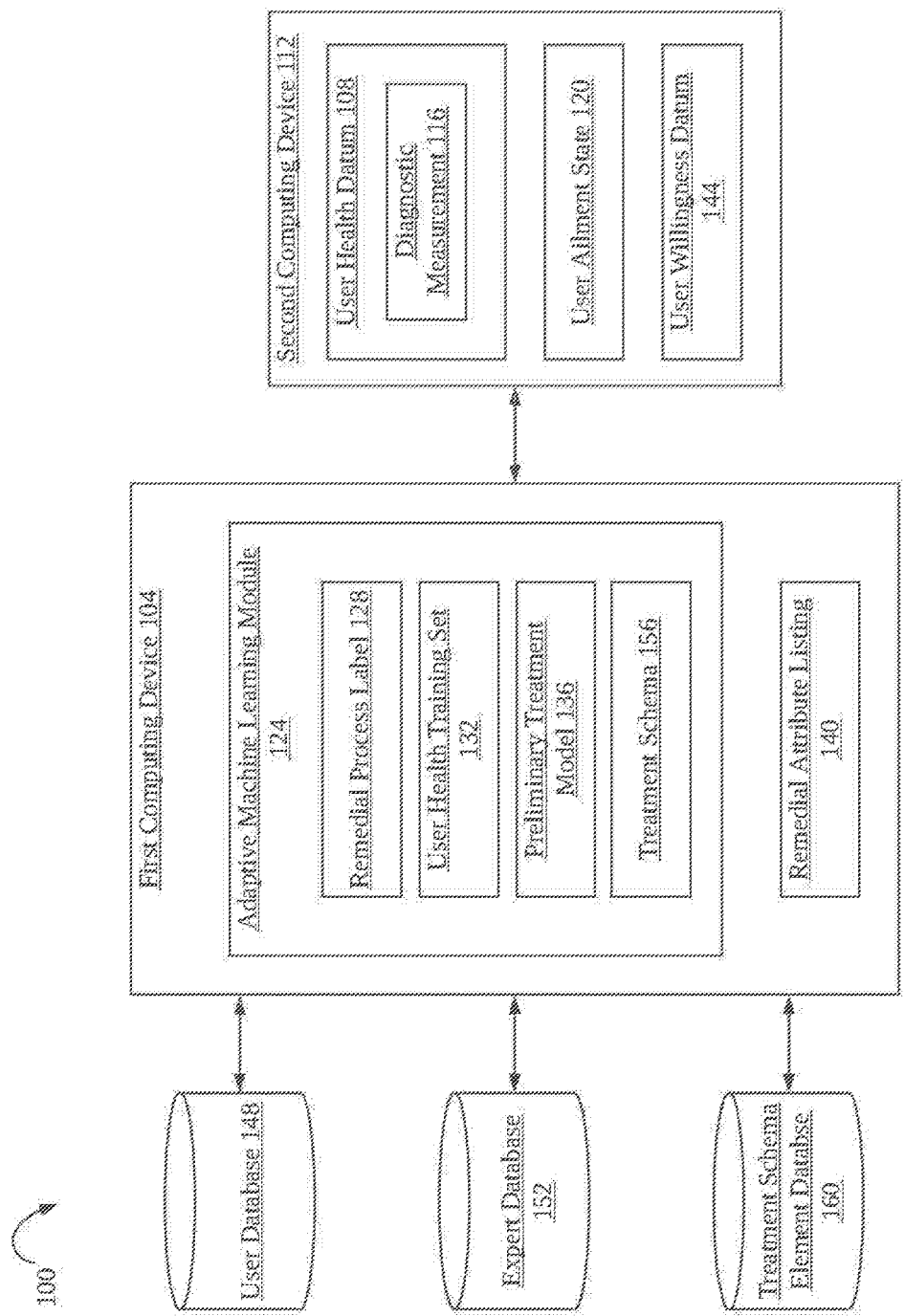
FIG. 1 is a block diagram illustrating an exemplary embodiment of a system for selecting a treatment schema based on user willingness.

Referring now to FIG. 1, an exemplary embodiment of system 100 for selecting a treatment schema based on user willingness with at least a first computing device 104 is illustrated. System 100 includes at least a first computing device. At least a first computing device may include any computing device as described above for any kind of electronic device with data processing capabilities in this disclosure. Computing device may include, be included in, and/or communicate with a mobile device such as a mobile telephone or smartphone. At least a first computing device may include a single computing device operating independently, or may include two or more computing device operating in concert, in parallel, sequentially or the like; two or more computing devices may be included together in a single computing device or in two or more computing devices. At least a first computing device may interact with one or more additional devices as described below in further detail via a network interface device. Network interface device may be utilized for connecting at least a first computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. At least a first computing device may include but is not limited to, for example, a computing device or cluster of computing devices in a first location and a second computing device or cluster of computing devices in a second location. At least a first computing device may include one or more computing devices dedicated to data storage, security, distribution of traffic for load balancing, and the like. At least a first computing device may distribute one or more computing tasks as described below across a plurality of computing devices of computing device, which may operate in parallel, in series, redundantly, or in any other manner used for distribution of tasks or memory between computing devices. At least a first computing device may be implemented using a "shared nothing" architecture in which data is cached at the worker, in an embodiment, this may enable scalability of system 100 and/or computing device.

With continued reference to FIG. 1, at least a first computing device may be designed and/or configured to perform any method, method step, or sequence of method steps in any embodiment described in this disclosure, in any order and with any degree of repetition. For instance, at least a first computing device may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. At least a first computing device may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, system 100 and components herein may include and/or communicate with a non-transitory computer readable medium, which may include any non-transitory memory as described in this disclosure; memory and/or non-transitory computer readable medium may store instructions to perform any method, method step, or sequence of method steps in any embodiment described in this disclosure, in any order and with any degree of repetition, as further described above in reference to at least a first computing device. In an embodiment, a non-transitory machine-readable storage medium contains machine-executable instructions for performing a method of selecting a treatment schema based on user willingness with at least a first computing device including a first set of machine-executable instructions for receiving at least a user constitutional datum from at least a second computing device indicating at least a diagnostic measurement, receiving at least a user ailment state from at least a second computing device indicating a current or future ailment, determining, with adaptive machine learning, at least a remedial process label using the at least a user constitutional datum and the at least a user ailment state, deriving a remedial attribute list, wherein the remedial attribute list further comprises a plurality of remedial attribute list entries including a remedial process label value indicating a degree of importance of at least a remedial process label and at least a user willingness level value indicating a numerical measure of a user willingness, generating a plurality of treatment schemas, wherein each treatment schema of the plurality of treatment schemas includes a treatment schema attribute listing having a plurality of treatment schema attribute listing entries, the plurality of treatment schema attribute listing entries includes an attribute listing entry corresponding to each remedial attribute list entry of the plurality of remedial attribute list entries, and each treatment schema attribute listing entry indicates a degree of impact on a factor represented by a remedial attribute list entry, selecting a treatment schema from the plurality of treatment schemas, wherein selecting the treatment schema further comprises generating a loss function of the plurality of treatment schemas and the remedial attribute list, minimizing the loss function, and selecting the treatment schema from the plurality of treatment schemas as a function of minimizing the loss function, and transmitting the selected treatment schema to the at least a second computing device. Each of the above-described steps may be performed in any way described anywhere in this disclosure.

Still referring to FIG. 1, at least a first computing device 104 is designed and configured to receive at least a user constitutional datum 108 from at least a second computing device 112 indicating at least a diagnostic measurement 116. "At least a second computing device 112" includes an electronic device in any configuration as described for at least a first computing device 104 above. For example, at least a second computing device 112 may transmit data received by at least a first computing device 104 related to a patient and be operated by a constitutionalcare professional responsible for monitoring, diagnosing, and/or treating such patient such as a hospital computer workstation or medical device. A medical professional may include, for example, a doctor, nurse, therapist, psychologist, medical technologist, or the like. As another example, at least a second computing device 112 may transmit data received by at least a first computing device 104 related to a patient and be operated by such patient such as a personal mobile device. "At least a user constitutional datum" as used in this disclosure, is an element of data describing information relevant to human subject's state of constitutional, including without limitation symptoms, conditions, prognoses, test results, concerns, reasons for a visit to a constitutionalcare professional, personal stories and/or information concerning the human subject's interests, relationships to other people, informal and/or formal personal or constitutional support groups or persons, or the like. At least a user constitutional datum 108 includes, without limitation, at least a diagnostic measurement 116. "At least a diagnostic measurement," or "diagnostic," as used herein, is one or more medical tests related to an individual for detecting, diagnosing, or monitoring ailments (i.e. diseases), disease processes, susceptibility, or to determine a course of treatment for a disease. At least a diagnostic measurement 116 may relate to medical tests run in the medical laboratory in the departments of clinical chemistry, hematology, blood bank, urinalysis, microbiology, molecular diagnostics, or the like; at least a diagnostic measurement 116 may include a physically extracted sample as described in further detail below. At least a diagnostic measurement 116 may include any element and/or elements of data suitable for use as an element of physiological state data. Physiological state data may include any data indicative of a person's physiological state; physiological state may be evaluated with regard to one or more measures of constitutional of a person's body, one or more systems within a person's body such as a circulatory system, a digestive system, a nervous system, or the like, one or more organs within a person's body, and/or any other subdivision of a person's body useful for diagnostic or predictive purposes. Physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data of at least a diagnostic measurement 116 may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin A1-C (HbA1c) levels. Physiological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline photohatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibrinogen, plasma cystatin C, and/or brain natriuretic peptide.

Continuing to refer to FIG. 1, physiological state data of at least a diagnostic measurement 116 may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data of at least a diagnostic measurement 116 may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function and pain.

Continuing to refer to FIG. 1, at least a diagnostic measurement 116 may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices; for instance, user patterns of purchases, including electronic purchases, communication such as via chatrooms or the like, any textual, image, video, and/or data produced by the subject, any textual image, video and/or other data depicting and/or describing the subject, or the like.

Still referring to FIG. 1, at least a diagnostic measurement 116 may include genomic data, including deoxyribonucleic acid (DNA) samples and/or sequences, such as without limitation DNA sequences contained in one or more chromosomes in human cells. Genomic data may include telomere lengths. Genomic data may include epigenetic data including data describing one or more states of methylation of genetic material. At least a diagnostic measurement 116 may include transcriptomic data, without limitation, ribonucleic acid (RNA) samples and/or sequences, such as samples and/or sequences of messenger RNA (mRNA) or the like taken from human cells. At least a diagnostic measurement 116 may include proteomic data, which as used herein is data describing all proteins produced and/or modified by an organism, colony of organisms, or system of organisms, and/or a subset thereof. At least a diagnostic measurement 116 may include molecular biology data, such data concerning the molecular basis of biological activity between biomolecules in the various systems of a cell, including the interactions between DNA, RNA, proteins and their biosynthesis, as well as the regulation of these interactions. Techniques relating to molecular biology data may include molecular cloning, polymerase chain reaction (PCR), gen electrophoresis, macromolecule blotting and probing (i.e. southern blotting, northern blotting, western blotting, eastern blotting), microarrays, allele-specific oligonucleotide (ASO), and the like. At least a diagnostic measurement 116 may include cell biology data, such data concerning the structure and function of a cell, as well as the physiological properties, metabolic processes, signaling pathways, life cycle, chemical composition, and interactions of the cell with their environment. Cell biology data may include information related to cellular processes such as active transport, passive transport, autophagy, adhesion, movement, regulatory signaling, mitosis, meiosis, DNA repair, metabolism, or the like.

With continued reference to FIG. 1, at least a diagnostic measurement 116 may include data concerning microbiological data, such as data related to organisms living on or within a person. Microbiological data may include clinical test results related to bacteriology, mycology, virology, parasitology, immunology, serology and the like. At least a diagnostic measurement 116 may include microbiome data relating to the microbiome of a person, which as used herein includes any data describing any microorganism and/or combination of microorganisms living on or within a person, including without limitation genomic data, transcriptomic data, proteomic data, and/or any other metabolic or biochemical data useful for analysis of the effect of such microorganisms on other diagnostic measurements 116, ailment states, or the like of a person as described in further detail below. At least a diagnostic measurement 116 may include any data as described above which may be used for describing any multicellular organism living in or on a person including any pathogenic and/or symbiotic organism living in or on a person; non-limiting examples may include mites, nematodes, flatworms, roundworms, bacteria, fungi, viruses, or the like.

With continued reference to FIG. 1, at least a diagnostic measurement 116 may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. A medical professional may enter such descriptions of a person's physiological state as well.

With continued reference to FIG. 1, at least a diagnostic measurement 116 may include data from a physically extracted sample, where a "physically extracted sample" as used in this disclosure is a sample obtained by removing and analyzing tissue, and/or fluid from a person. Physically extracted sample may include without limitation a blood sample, a tissue sample, a buccal swab, a mucous sample, a stool sample, a urine sample, a hair sample, a fingernail sample, or the like. As a further non-limiting example, a physically extracted sample may include a genetic sample. A genetic sample may include DNA, RNA, and/or proteomic data of a person as described above. A physically extracted sample may include an epigenetic sample, a proteomic sample, a tissue sample, a biopsy, and/or any other physically extracted sample. A physically extracted sample may be in the form of extraction from a person for analysis of any of the non-limiting example as described above and throughout this disclosure for at least a diagnostic measurement 116.

With continued reference to FIG. 1, at least a diagnostic measurement 116 may include a signal from at least a sensor configured to detect physiological data of a user and recording the at least a diagnostic measurement 116 as a function of the signal. At least a sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. At least a sensor may include any electromagnetic sensor, including without limitation electroencephalographic sensors, magnetoencephalographic sensors, electrocardiographic sensors, electromyographic sensors, or the like. At least a sensor may include a temperature sensor. At least a sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. At least a sensor may detect any hematological parameter including blood oxygen level, pulse rate, heart rate, pulse rhythm, and/or blood pressure. At least a sensor may be a part of system 100 or may be a separate device in communication with system 100.

Still referring to FIG. 1, at least a diagnostic measurement 116 may include data describing one or more test results, including results of mobility tests, stress tests, dexterity tests, genetic tests, electromyographic tests, biopsies, radiological tests, genetic tests, and/or sensory tests. Any data and/or data used to generate at least a diagnostic measurement 116 of at least a user constitutional datum 108 may be analyzed using machine learning as described in this disclosure below. Examples of at least a diagnostic measurement 116 and at least a user constitutional datum 108 described in this disclosure are presented for illustrative purposes only and are not meant to be exhaustive. Persons skilled in the art, upon reviewing the entirety of this disclosure, will be aware of various additional examples of at least a diagnostic measurement 116 and at least a user constitutional datum 108 that may be used consistently with descriptions of systems and methods as provided in this disclosure. At least a diagnostic measurement 116 of user within at least a user constitutional datum 108 may be added to a database, as described in further detail below.

Continuing to refer to FIG. 1, at least a first computing device 104 is designed and configured to receive at least a user ailment state 120 from at least a second computing device 112 indicating a current or future ailment. "At least as user ailment state," as described herein, is an element of data identifying and/or describing a current, incipient, or probable future ailment (medical condition) affecting a person; ailment may include a particular disease, one or more symptoms associated with a syndrome, a syndrome, and/or any other measure of current or future constitutional and/or constitutionally aging. At least a user ailment state 120 may be associated with a physical and/or somatic condition, a mental condition such as a mental illness, neurosis, or the like, or any other condition affecting human constitutional that may be associated with one or more elements of physiological state data as described in further detail below. Conditions associated with user ailment states may include, without limitation one or more diseases, defined for purposes herein as conditions that negatively affect structure and/or function of part or all of an organism. Conditions associated with user ailment states may include, without limitation, acute or chronic infections, including without limitation infections by bacteria, archaea, viruses, prions, single-celled eukaryotic organisms such as amoeba, paramecia, trypanosomes, plasmodia, *leishmania*, and/or fungi, and/or multicellular parasites such as nematodes, arthropods, fungi, or the like. User ailment states may be associated with one or more immune disorders, including without limitation immunodeficiencies and/or auto-immune conditions. User ailment states may be associated with one or more metabolic disorders. User ailment states may be associated with one or more endocrinal disorders. User ailment states may be associated with one or more cardiovascular disorders. User ailment states may be associated with one or more respiratory disorders. User ailment states may be associated with one or more disorders affecting connective tissue. User ailment states may be associated with one or more digestive disorders. User ailment states may be associated with one or more neurological disorders such as neuromuscular disorders, dementia, or the like. User ailment states may be associated with one or more disorders of the excretory system, including without limitation nephrological disorders. User ailment states may be associated with one or more liver disorders. User ailment states may be associated with one or more disorders of the bones such as osteoporosis. User ailment states may be associated with one or more disorders affecting joints, such as osteoarthritis, gout, and/or rheumatoid arthritis. User ailment states be associated with one or more cancers, including without limitation carcinomas, lymphomas, leukemias, germ cell tumor cancers, blastomas, and/or sarcomas. User ailment states may include descriptors of latent, dormant, and/or apparent disorders, diseases, and/or conditions. User ailment states may include descriptors of conditions for which a person may have a higher than average probability of development, such as a condition for which a person may have a "risk factor"; for instance, a person currently suffering from abdominal obesity may have a higher than average probability of developing type II diabetes. The above-described examples are presented for illustrative purposes only and are not intended to be exhaustive. Persons skilled in the art, upon reviewing the entirety of this disclosure, will be aware of various additional examples of conditions that may be associated with at least a user ailment state 120 as described in this disclosure.

Continuing to refer to FIG. 1, at least a first computing device 104 is designed and configured to determine, using an adaptive machine learning module 124, at least a remedial process label 128 using the at least a user constitutional datum 108 and the at least a user ailment state 120. "At least a remedial process label" as described herein is an identifier, which may include any form of identifier suitable for use as at least a user constitutional datum 108 as described above, identifying a process that tends to improve a physical condition of a user (patient), where a physical condition of a patient may include, without limitation, any physical condition identifiable using at least a user constitutional datum 108 and/or at least a user ailment state 120. Remedial processes may include, without limitation, exercise programs, including amount, intensity, and/or types of exercise recommended. Remedial processes may include, without limitation, dietary or nutritional recommendations based on at least a user constitutional datum 108 including nutritional content, digestibility, or the like. Remedial processes may include one or more medical procedures. Remedial processes may include one or more physical, psychological, or other therapies. Remedial processes may include one or more medications. Persons skilled in the art, upon reviewing the entirety of this disclosure, will be aware of various processes that may be used as remedial processes consistently with this disclosure.

With continued reference to FIG. 1, an adaptive machine learning module 124 may be implemented as any electronic device with a processor as described herein, including without limitation any device suitable for use as at least a first computing device 104, and/or as any hardware and/or software module incorporated in, operating on, or in communication with such a computing device. Adaptive machine learning module 124 performs at least a machine learning process. A machine learning process is a process that automatedly uses a body of data known as "training data" and/or a "training set" to generate an algorithm that will be performed by a computing device/module to produce outputs given data provided as inputs; this is in contrast to a non-machine learning software program where the commands to be executed are determined in advance by a user and written in a programming language. Machine learning may perform determinations, classification, and/or analysis steps, methods, processes, or the like as described in this disclosure using various processes. Adaptive machine learning module 124 performs adaptive machine learning processes. "Adaptive machine learning" as described herein includes a process that changes its behavior at the time it is run, based on information available and on a priori defined criterion. Such information could be the story of recently received data, information on the available computing device, or other run-time acquired (or a priori known) information related to the environment in which it operates. Adaptive machine learning may use adaptive algorithms such as, for example, the Widrow-Hoff's least mean squares, stable partition, adaptive sort, and/or any other algorithm classified as an adaptive algorithm used in machine learning. In an embodiment, adaptive machine learning module 124 selects an appropriate machine learning algorithm for determining at least a remedial process label 128 based on the information contained in the inputs of at least a user constitutional datum 108 and the at least a user ailment state 120.

With continued reference to FIG. 1, "training data," as used herein, is data containing correlation that a machine learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine learning algorithms, and/or automated association of data in the data entry with descriptors or into a given format. The ability to categorize data entries automatedly may enable the same training data to be made applicable for two or more distinct machine learning algorithms as described in further detail below. Training data used by adaptive machine learning module 124 may correlate any input data as described in this disclosure to any output data as described in this disclosure.

Still referring to FIG. 1, adaptive machine learning module 124 may be designed and configured to create a machine learning model using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 1, machine learning algorithms of adaptive machine learning module 124 may include, without limitation, linear discriminant analysis. Machine learning algorithm may include quadratic discriminate analysis. Machine learning algorithms may include kernel ridge regression. Machine learning algorithms may include support vector machines, including without limitation support vector classification-based regression processes. Machine learning algorithms may include stochastic gradient descent algorithms, including classification and regression algorithms based on stochastic gradient descent. Machine learning algorithms may include nearest neighbors algorithms. Machine learning algorithms may include Gaussian processes such as Gaussian Process Regression. Machine learning algorithms may include cross-decomposition algorithms, including partial least squares and/or canonical correlation analysis. Machine learning algorithms may include naïve Bayes methods. Machine learning algorithms may include algorithms based on decision trees, such as decision tree classification or regression algorithms. Machine learning algorithms may include ensemble methods such as bagging meta-estimator, forest of randomized tress, AdaBoost, gradient tree boosting, and/or voting classifier methods. Machine learning algorithms may include neural net algorithms, including convolutional neural net processes.

Still referring to FIG. 1, other models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data.

Still referring to FIG. 1, machine learning algorithms of adaptive machine learning module 124 may include supervised machine learning algorithms. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include user constitutional data 108 and/or user ailment state 120 information as inputs, remedial process label 128 information as outputs, and a scoring function representing a desired form of relationship to be detected between inputs and outputs; scoring function may, for instance, seek to maximize the probability that a given input and/or combination of input elements are associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine learning algorithms that may be used to determine relation between inputs and outputs.

Still referring to FIG. 1, supervised machine learning processes of adaptive machine learning module 124 may include classification algorithms, defined as processes whereby a computing device derives, from training data, a model for sorting inputs into categories or bins of data. Classification may be performed using, without limitation, linear classifiers such as without limitation logistic regression and/or naive Bayes classifiers, nearest neighbor classifiers, support vector machines, decision trees, boosted trees, random forest classifiers, and/or neural network-based classifiers.

Still referring to FIG. 1, machine learning processes of adaptive machine learning module 124 may include unsupervised processes. An unsupervised machine learning process, as used herein, is a process that derives inferences in datasets without regard to labels; as a result, an unsupervised machine learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 1, machine learning processes of adaptive machine learning module 124 as described in this disclosure may be used to generate machine learning models. A machine learning model, as used herein, is a mathematical representation of a relationship between inputs and outputs, as generated using any machine learning process including without limitation any process as described above, and stored in memory; an input is submitted to a machine learning model once created, which generates an output based on the relationship that was derived. For instance, and without limitation, a linear regression model, generated using a linear regression algorithm, may compute a linear combination of input data using coefficients derived during machine learning processes to calculate an output datum. As a further non-limiting example, a machine learning model may be generated by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

A lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data. Heuristic may include selecting some number of highest-ranking associations and/or training data elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine learning algorithms as described in further detail below.

With continued reference to FIG. 1, determining the at least a remedial process label 128 by an adaptive machine learning module 124 may include receiving training data correlating at least a user constitutional datum 108 of at least a user ailment state 120 to at least a remedial process label 128. "Correlation" in training data may include any relation established therein linking one datum to another, such as inclusion together in a data element, row, column, cell, or the like, and/or by giving each a common indicator and/or label indicative of their correlation in data used to create and/or compile training data. In an embodiment, training data may be received from a database, as described below, that contains information on a plurality of diagnostic tests, illnesses, and recommended treatments for such illnesses; for example, training data may receive a plurality of user constitutional datums 108 indicating elevated glycated hemoglobin (A1C) levels, elevated fasting blood glucose levels, and obesity, with at least a user ailment state 120 indicating type 2 diabetes; such information being correlated to at least a remedial process label 128 indicating ways in which to alleviate such mentioned negative constitutional factors such as weight loss, regular exercise, constitutionally eating, and blood sugar monitoring.

With continued reference to FIG. 1, determining the at least a remedial process label by adaptive machine learning module 124 may include receiving training data correlating at least a user constitutional datum 108 of at least a user ailment state 120 and/or at least a remedial process label 128 to variances between actuarial life expectancy datum and actual mortality dates. "Actuarial life expectancy" is defined as a probable age of death, as predicted using any actuarial method and/or table, and/or an interval from a date such as the present date to the probable age of death; actuarial methods may include looking up and/or calculating a user's life expectancy using date of birth and/or demographic information about the user such as sex, ethnicity, geographic location, nationality, or the like. A "user age factor," as used in this disclosure, is a factor that may be multiplied by a user's chronological age to reflect an effect that at least a user constitutional datum 108 has on the user's effective age. A user's "chronological age," as defined in this disclosure, is an age of the user as measured in years, or other units of time, from the date of the user's birth to the date of the measurement, where a "date" may include any calendar date, Julian date, or the like. A chronological age may be used to project a user's actuarial life expectancy. "Actuarial life expectancy datum," as used herein, is a datum indicating an age of death of a subject person, as predicted by reference to actuarial calculations and/or tables, calculations may include prediction of a variance from actuarial life expectancy for a given person, where a "variance from actuarial life expectancy" is a difference between an actuarial life expectancy for that person and a projected number of years until death as determined based on at least a measure of at least a user constitutional datum 108 of at least a user ailment state 120 and/or at least a remedial process label 128. A difference between these values may be added to a user chronological age and then divided by the user chronological age to calculate a "raw" score, which may represent an estimated effect of at least a user constitutional datum 108 of at least a user ailment state 120 and/or at least a remedial process label 128 on life expectancy without regard for relatedness to other variables; a raw score may then be multiplied by a weight to determine the user age factor, where the weight may account for interrelatedness between at least a user constitutional datum 108 of at least a user ailment state 120 and/or at least a remedial process label 128 and other measures used to calculate user effective age as described herein. Indications of actuarial life expectancy datum may be achieved, without limitation, using a datum containing actuarial life expectancy and/or a datum that may be used to determine actuarial life expectancy.

With continued reference to FIG. 1, "actual mortality date" as used herein, is a date on which a person actually died; elements or entries in training data may include data concerning people who have died, enabling actual mortality date to be determined. An actual mortality date may include a measure of time between the date of a given at least a user constitutional datum 108 of at least a user ailment state 120 and/or at least a remedial process label 128 measurement and the death of the person with regard to whom the measurement was taken, which may be represented as a calendar date and/or as a number of years after the date of measurement. A "variance between actuarial life expectancy datum and actual mortality date" may include a difference between a life expectancy as determined by actuarial life expectancy and actual mortality date, which may be determined by any suitable measure of difference between numerical quantities, including without limitation by subtraction. "Correlation" in a training data set, as used in this context, may include any relation established therein linking one datum to another, including inclusion together in a data element, row, column, cell, or the like, and/or by giving each a common indicator and/or label indicative of their correlation in data used to create and/or compile training data. Correlation of at least a measure of at least a user constitutional datum 108 of at least a user ailment state 120 and/or at least a remedial process label 128 to variances between actuarial life expectancy data and actual mortality dates may be accomplished by correlating to a calculated variance, to a factor based on the calculated variance, which may include user age factor; alternatively or additionally, such correlation may indicate correlation to actuarial life expectancy datum and/or a dataset suitable for looking up actuarial life expectancy, and to actual mortality date, or any other set of data from which such a variance may be deduced. In other words, and by way of illustration only, an actual mortality date per se may not be in a training set entry; instead it might be a difference between actuarial and actual life expectancies, a life expectancy plus chronological age (from which variance may be calculated), or the like.

Still referring to FIG. 1, adaptive machine learning module 124 may perform one or more processes to modify and/or format training data to produce a user constitutional training set 132. User constitutional training set 132 may include a plurality of entries, each entry correlating at least a diagnostic measurement 116 of at least a user constitutional datum 108 of at least a user ailment state 120 and/or a change in at least a diagnostic measurement 116 of at least a user constitutional datum 108 of at least a user ailment state 120, to at least a remedial process label 128. At least a first computing device 104 may, without limitation, modify entries in training data to contain consistent forms of remedial process label, for instance so that a regression process or other supervised machine learning process may operate without converting data to particular forms during operation; alternatively, supervised machine learning process may perform standardization calculations during operation. Other modifications may include receiving a training set correlating one or more diagnostics to at least a remedial process label 128, where correlations and entries may be implemented as described above; for instance, training data relating at least a user constitutional datum 108 of at least a user ailment state 120 and/or a change in at least a user constitutional datum 108 of at least a user ailment state 120, to at least a remedial process label 128, but a training set relating one or more additional diagnostics to at least a remedial process label 128 may be received. At least a first computing device 104 may use one or more additional machine learning processes to create user constitutional training set 132 relating at least a diagnostic measurement 116 of at least a user constitutional datum 108 of at least a user ailment state 120 to at least a remedial process label 128 by modifying training data relating one or more additional diagnostics to at least a remedial process label 128. For instance, and without limitation, adaptive machine learning module 124 may perform an unsupervised machine learning process on training data correlating at least a diagnostic measurement 116 of at least a user constitutional datum 108 measure with additional diagnostics, which may be any diagnostic; unsupervised machine learning may be used to cluster at least a diagnostic measurement 116 of at least a user constitutional datum 108 and/or a change in at least a diagnostic measurement 116 of at least a user constitutional datum 108 with one or more other diagnostics, for instance to identify one or more additional diagnostics that are highly correlated with the at least a user ailment state 120. At least a first computing device 104 may then modify the training data to create user constitutional training set 132 by replacing one or more additional diagnostics in each entry of the training data with at least a diagnostic measurement 116 of at least a user constitutional datum 108 that is correlated therewith by the unsupervised machine learning set. In an embodiment, this approach may make it possible to draw upon training data relating at least a diagnostic measurement 116 of at least a user constitutional datum 108 of at least a user ailment state 120 to at least a remedial process label 128 indicating ways in which ailments may be alleviated. In an embodiment, the one or more additional diagnostics may include a first measure of at least a user constitutional datum 108, and the at least a diagnostic measurement 116 of at least a user constitutional datum 108 may include a second diagnostic measurement 116 of at least a user constitutional datum 108, enabling replacement of a first diagnostic measurement 116 of at least a user constitutional datum 108 with a second diagnostic measurement 116 of at least a user constitutional datum 108 in first user constitutional training set 132.

With continued reference to FIG. 1, where user constitutional training set 132 correlates at least a diagnostic measurement 116 of at least a user constitutional datum 108 of at least a user ailment state 120 and/or a change in at least a diagnostic measurement 116 of at least a user constitutional datum 108 of at least a user ailment state 120 to at least a remedial process label 128, adaptive machine learning module 124 may use the user constitutional training set 132 for generating, using a supervised machine learning process, a preliminary treatment model 136 that receives at least a user constitutional datum 108 of at least a user ailment state 120 and/or a change in at least a user constitutional datum 108 of at least a user ailment state 120 as inputs and produces an output representing at least a remedial process label 128, where preliminary treatment model 136 may include any machine-learning model. Providing an output "representing" at least a remedial process label 128 means an output from which a value can be calculated, such as providing a raw score, for instance as described above. For example, adaptive machine learning module 124 may generate, using a supervised machine learning process, a preliminary treatment model 136 that receives at least a user constitutional datum 108 of at least a user ailment state 120 and/or a change in at least a user constitutional datum 108 of at least a user ailment state 120 as inputs and produces an output representing at least a remedial process label 128. Adaptive machine learning module 124 may then determine the at least a remedial process label 128 using the at least a user ailment state 120 and/or a change in at least a user constitutional datum 108 of at least a user ailment state 120 and the preliminary treatment model 136, by inputting the at least a diagnostic measurement 116 of the at least a user constitutional datum 108 and/or change in the at least a diagnostic measurement 116 of the at least a user constitutional datum 108 into the preliminary treatment model 136, and receiving an output; output may be a raw score, which may represent an estimated effect of the at least a diagnostic measurement 116 and/or change in the at least a diagnostic measurement 116 of the at least a user constitutional datum 108 on the at least a remedial process label 128 determination without regard for relatedness to other variables; a raw score may then be multiplied by a weight to determine the at least a remedial process label 128, where the weight may account for interrelatedness between at least a diagnostic measure 116 and/or change in the at least a diagnostic measurement 116 of at least a user constitutional datum 108 and other measures used to calculate at least a remedial process label 128 as described herein.

With continued reference to FIG. 1, where user constitutional training set 132 correlates at least a user constitutional datum 108 of at least a user ailment state 120 and/or at least a remedial process label 128 to variances between actuarial life expectancy datum and actual mortality dates, adaptive machine learning module 124 may use the user constitutional training set 132 for generating, using a supervised machine learning process, a preliminary treatment model 136 that receives at least a user constitutional datum 108 of at least a user ailment state 120 and/or at least a remedial process label 128 as inputs and produces an output representing variances between actuarial life expectancy datum and actual mortality dates, where preliminary treatment model 136 may include any machine-learning model. Providing an output "representing" a variance means an output from which a variance can be calculated, including providing the actuarial life expectancy and projected actual mortality date as two output elements, providing the difference between the actuarial life expectancy and a projected actual mortality date, and/or providing a raw score, for instance as described above. For example, adaptive machine learning module 124 may generate, using a supervised machine learning process, a preliminary treatment model 136 that receives at least a user constitutional datum 108 of at least a user ailment state 120 and/or at least a remedial process label 128 as inputs and produces an output representing a variance between actuarial life expectancy and a projected actual mortality date. Adaptive machine learning module 124 may then determine the variances between actuarial life expectancy datum and actual mortality dates using the at least a user constitutional datum 108 of at least a user ailment state 120 and/or at least a remedial process label 128 and the preliminary treatment model 136, by inputting the at least a user constitutional datum 108 of at least a user ailment state 120 and/or at least a remedial process label 128 into the preliminary treatment model 136, and receiving an output; output may be a raw score, which may represent an estimated effect of the at least a user constitutional datum 108 of at least a user ailment state 120 and/or at least a remedial process label 128 on the at least a variance determination between actuarial life expectancy datum and actual mortality dates without regard for relatedness to other variables; a raw score may then be multiplied by a weight to determine the variance between actuarial life expectancy datum and actual mortality dates, where the weight may account for interrelatedness between at least a user constitutional datum 108 of at least a user ailment state 120 and/or at least a remedial process label 128 and other measures used to calculate the variance between actuarial life expectancy datum and actual mortality dates as described herein. In an embodiment, adaptive machine learning module 124 calculates the effect of at least a user constitutional datum 108 of at least a user ailment state 120 and/or at least a remedial process label 128 on variances between actuarial life expectancy datum and actual mortality dates to output an amount of change in such variance due to each at least a user constitutional datum 108 of at least a user ailment state 120 and/or at least a remedial process label 128, or due to a degree of impact. A degree of impact, as used in this context, may include an amount of influence each at least a user constitutional datum 108 of at least a user ailment state 120 and/or at least a remedial process label 128 has on life expectancy represented as a numerical amount; for example, larger numbers indicating a large positive impact on life expectancy, small numbers indicating a small positive impact on life expectancy, negative numbers indicating a negative impact on life expectancy, and the like. A degree of impact may also factor in user constitutional training set 132 that correlates at least a user constitutional datum 108 of at least a user ailment state 120 and/or at least a remedial process label 128 to variances between actuarial life expectancy datum and actual mortality dates, as described above.

With continued reference to FIG. 1, adaptive machine learning module 124 may use one or more additional machine learning processes to create user constitutional training set 132 relating at least a user constitutional datum 108 and/or changes in at least a user constitutional datum 108 to at least a remedial process label 128 relating one or more additional diagnostics to the at least a remedial process label 128. For instance, and without limitation, adaptive machine learning module 124 may perform an unsupervised machine learning process on training data correlating at least a user constitutional datum 108 and/or changes in at least a user constitutional datum 108 with at least a user ailment state 120, which may be inclusive of any diagnostic; unsupervised machine learning may be used to cluster at least a user constitutional datum 108 and/or changes in at least a user constitutional datum 108 with at least a user ailment state 120 and one or more other diagnostics, for instance to identify one or more additional diagnostics that are highly correlated with at least a user constitutional datum 108 and/or changes in at least a user constitutional datum 108 and at least a user ailment state 120. Adaptive machine learning module 124 may then modify the training data to generate user constitutional training set 132 by replacing one or more additional diagnostics in each entry of the training data with at least a user constitutional datum 108 and/or changes in at least a user constitutional datum 108 and at least a user ailment that is correlated therewith by the unsupervised machine learning set. In an embodiment, this may involve generating the training data correlating the at least a user constitutional datum 108 and/or change in the at least a user constitutional datum 108 and the at least a user ailment state 120 to the at least a remedial process label 128 using the training data correlating the at least a user constitutional datum 108 and/or change in the at least a user constitutional datum 108 of at least a user ailment state 120 and the identified correlation between the at least a user constitutional datum 108 and/or change in the at least a user constitutional datum 108 and the at least a user ailment state 120. In an embodiment, this approach may make it possible to draw upon training data relating one or more diagnostics of at least a user ailment state 120 to measures of at least a user constitutional datum 108 and/or changes in at least a user constitutional datum 108, as data describing actual dates of alleviated ailments by remedial processes 128 may take years to collect, whereas data relating an additional diagnostic of at least a user ailment state 120 to at least a measure of at least a user constitutional datum 108 and/or changes in at least a user constitutional datum 108 may be collected rapidly.

With continued reference to FIG. 1, at least a first computing device 104 is designed and configured to derive a remedial attribute list 140 from at least a user willingness datum 144, where the remedial attribute list 140 further includes a plurality of remedial attribute list 140 entries including at least a remedial process label 128 value indicating a degree of importance of at least a remedial process, and a user willingness level value indicating a numerical measure of a user willingness. "User willingness datum," as used herein, includes an element of data describing a user's willingness to partake of one or more remedial processes; user willingness datum may include at least an entry of commitments from a user that relate to achieving a constitutionally state from a state of illness as indicated by at least a user constitutional datum 108, or to at least a user ailment state 120. At least a user willingness datum 144 may be received from at least a second computing device 112. At least a user willingness datum 144 may contain information about time commitments the user has to a specific treatment, readiness to try certain foods or fitness routines, restrictions on foods due to distastes or allergies, readiness to take certain medications, reservations about taking certain medications, or the like; all information contained within at least a user willingness datum 144 to be used for creating treatment plans curated towards commitments and preferences of a user. At least a user willingness datum 144 includes at least a user willingness level value; at least a user willingness level value being an assigned numerical value of importance for each entry within at least a user willingness datum 144. At least a user willingness level may, for example, be entered by a user on a scale of 1-10, such that 1 would be of minor priority and 10 being the highest priority commitment of at least a user willingness datum 144. In one embodiment, a supervised machine learning model may use training data correlating input data describing both at least a user constitutional datum 108 and at least a remedial process label 128, in addition to at least a user willingness datum 144, to output data representing variances between actuarial life expectancy and actual mortality date, and generating, using any suitable supervised machine learning process as described above, a model that takes as inputs combinations of user constitutional datums 108 and/or remedial process labels 128 and user willingness datums 144 and outputs an impact, as described above, such as an impact on variances between life expectancy and actual mortality dates, that is specific to willingness of a user. Examples relating to at least a user willingness datum 144 are below.

Continuing to refer to FIG. 1, a "remedial attribute list" is a data structure that represents a quantitative measure of a degree of importance a user places on each of a plurality of user willingness aimed at remediating at least a user ailment state 120 and/or at least a user constitutional datum 108 of at least a user ailment state 120, including data mentioned that may be contained in at least a user willingness datum 144, user effective age or equivalently increase in life expectancy, and/or one other distinct priority, as described below in reference to user database 148. Remedial attribute list 140 as defined in this disclosure, may be represented as an n-tuple of values, where n is at least two values, as described in further detail below; values may be stored and/or manipulated in any suitable data structure, including without limitation a variable or fixed-length array, vector, linked list, or the like. Each value of n-tuple of values may represent a measurement or other quantitative value associated with a given category of data, or attribute, examples of which are provided in further detail below; an attribute listing (i.e. a vector), may be represented, without limitation, in n-dimensional space using an axis per category of value represented in n-tuple of values, such that an attribute listing has a geometric direction characterizing the relative quantities of attributes in the n-tuple as compared to each other. Two attribute listings may be considered equivalent where their directions, and/or the relative quantities of values within each attribute listing as compared to each other, are the same; thus, as a non-limiting example, an attribute listing represented as [5, 10, 15] may be treated as equivalent, for purposes of this disclosure, as an attribute listing represented as [1, 2, 3]. Attribute listing may be more similar where their directions are more similar, and more different where their directions are more divergent; however, attribute listing similarity may alternatively or additionally be determined using averages of similarities between like attributes, or any other measure of similarity suitable for any n-tuple of values, or aggregation of numerical similarity measures for the purposes of loss functions as described in further detail below. Any attribute listing as described herein may be scaled, such that each attribute listing represents each attribute along an equivalent scale of values. Each attribute listing may be "normalized," or divided by a "length" attribute, such as a length attribute l as derived in vector geometry using a Pythagorean norm: $l=\sqrt{\Sigma_{i=0}^{n} a_i^2}$, where $a_i$ is attribute number i of the attribute listing. Scaling and/or normalization may function to make attribute listing comparison independent of absolute quantities of attributes, while preserving any dependency on similarity of attributes; this may, for instance be advantageous where each attribute listing represents a weighing of user priorities, and/or is to be compared to such a weighing of user priorities. Each remedial attribute list 140 entry includes a remedial process label value; a remedial process label value being an assigned numerical value of importance for each entry within a remedial attribute list 140. A remedial process label value may, for example, be entered by a user on a scale of 1-10, such that 1 would be of minor priority and 10 being the highest priority of remediating at least a user ailment state 120, at least a user constitutional datum 108 of at least a user ailment state 120, and/or an aspect of at least a user ailment state 120.

Continuing to refer to FIG. 1, remedial attribute list 140 includes a plurality of remedial attribute list 140 entries, which are attributes of user remedial attribute list 140 as described above. Plurality of remedial attribute list 140 entries includes a remedial process label value indicating a degree of importance of remedial process label 128. A plurality of remedial attribute list 140 entries includes at least a user willingness level value indicating a numerical measure of a user willingness, at least a user willingness level extracted from at least a user willingness datum 144 as described above. At least a user willingness level may include, for instance, an attribute indicating a degree of importance to user of cost of an action that may be taken to, for example, alleviate an ailment and improve life expectancy, such as a treatment schema and/or treatment schema element as described in further detail below. At least a user willingness level may include an attribute indicating a degree of importance to user of a detrimental habit; habit may be a factor multiplied by a user's chronological age to reflect an effect that a habit the user is engaged in has on the user's effective age. A detrimental habit may negatively impact a user's effective age. A habit a user is engaged in may be, for example: a nutritional habit, such as a daily consumption of sugar, fat, fiber, protein, or the like; an exercise habit, which may be measured in terms of a duration per day, week, or the like of cardiovascular exercise, resistance training exercise, or other exercise category, a number of steps per week taken, resting and/or total calorie consumption numbers, or the like; a substance abuse habit, including some measure of a dosage per period of time consumed of a harmful and/or addictive substance such as an opiate, alcohol, tobacco, stimulants such as cocaine, methamphetamine or the like, hallucinogens, narcotics, or other mood-altering chemicals; and/or a sleep habit, including a number of hours per night a user sleeps, a number of nights a user goes with less than a recommended amount of sleep, or the like. At least a user willingness level may include an attribute indicating a degree of importance to user of schedule commitment, where, for instance, a larger number may indicate a greater reluctance to schedule regular sessions, exercise programs, bedtimes, or the like. At least a user willingness level may include an attribute indicating a degree of importance to user of time commitment, which may include a numerical measure of a degree to which user is bothered by having to set aside a given amount of time in a week, day, month and/or year. At least a user willingness level may include an attribute indicating a degree of importance to user of a change in diet. Persons skilled in the art, upon reviewing the entirety of this disclosure, will be aware of various additional attributes that may be used for at least a user willingness level in remedial attribute list 140.

Referring again to FIG. 1, adaptive machine learning module 124 may derive user willingness level of remedial attribute list 140 by receiving at least a user input. For instance, a graphical user interface may display on at least a second computing device 112, such as a user device including a mobile phone, options to rate one or more willingness priorities absolutely and/or relatively to each other, for instance by providing a numerical rating scale with radio buttons and/or drop-down lists, sliders where a user may set relative importance along a continuum for at last a user willingness level value of a remedial attribute list 140 field, and/or textual entry fields wherein a user may enter numbers reflecting user's personal degree of importance for each field.

With continued reference to FIG. 1, deriving the remedial attribute list 140 by the at least a first computing device 104 may include assigning significance scores to the plurality of remedial attribute list 140 entries, ranking the plurality of remedial attribute list 140 entries as a function of the significance scores, transmitting a ranked remedial attribute list 140 to at least a second computing device 112 as a function of the ranked plurality of remedial attribute list 140 entries, receiving a user command modifying the ranked remedial attribute list 140, and deriving the remedial attribute list 140 using the ranked remedial attribute list 140 and the user command. "Significance scores" of remedial attribute list 140 entries or categories of remedial attribute list 140 entries may include labels and/or descriptors describing at least a user constitutional datum 108 and/or at least a user ailment state 120 to types of physiological state data that are identified as being of high relevance in identifying remedial process labels. As a non-limiting example, one or more categories may identify significant categories of physiological state data in at least a user constitutional datum 108 based on degree of diagnostic relevance to one or more impactful conditions and/or within one or more medical or public constitutional fields. For instance, a particular set of diagnostics, test results, and/or biochemical information may be recognized in a given medical field as useful for identifying various disease conditions or prognoses within a relevant field. For example, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss. Identification of significance may be performed by a language processing module, processes as described below in reference to FIG. 3.

With continued reference to FIG. 1, each category of a remedial attribute list 140 entry, relationship of such categories to at least a user constitutional datum 108 and/or at least a user ailment state 120, and/or category of at least a user constitutional datum 108 and/or at least a user ailment state 120 may be ranked according significance scores. Significance scores may be ranked; that is, all categories of physiological state data, relationships of such categories to remedial process labels, and/or categories of remedial process labels may be ranked according to significance scores, for instance by ranking categories of physiological state data, relationships of such categories to remedial process labels, and/or categories of remedial process labels higher according to higher significance scores and lower according to lower significance scores. Categories of physiological state data, relationships of such categories to remedial process labels, and/or categories of remedial process labels may be eliminated from current use if they fail a threshold comparison, which may include a comparison of significance score to a threshold number, a requirement that significance score belong to a given portion of ranking such as a threshold percentile, quartile, or number of top-ranked scores. Significance scores may be used to filter outputs as described in further detail below; for instance, where a number of outputs are generated and automated selection of a smaller number of outputs is desired, outputs corresponding to higher significance scores may be identified as more probable and/or selected for presentation while other outputs corresponding to lower significance scores may be eliminated. Alternatively or additionally, significance scores may be calculated per sample type; for instance, entries by experts, documents, published scientific papers, and/or descriptions of purposes of a given type of physiological test or sample collection as described herein may indicate that for that type of physiological test or sample collection a first category of physiological state data, relationship of such category to remedial process labels, and/or category of remedial process labels is significant with regard to that test, while a second category of physiological state data, relationship of such category to remedial process labels, and/or category of remedial process labels is not significant; such indications may be used to perform a significance score for each category of physiological state data, relationship of such category to remedial process labels, and/or category of remedial process labels is or is not significant per type of physiological sample, which then may be subjected to ranking, comparison to thresholds and/or elimination as described above. Entries by experts, documents, published scientific papers, and/or descriptions of purposes of a given type of physiological test or sample collection may be extracted from an expert database 152. Extraction of significance scores based on entries by experts, documents, and/or descriptions of purposes of a given type of physiological test or sample collection may be performed by a language processing module as described below in reference to FIG. 3.

Figure 3:
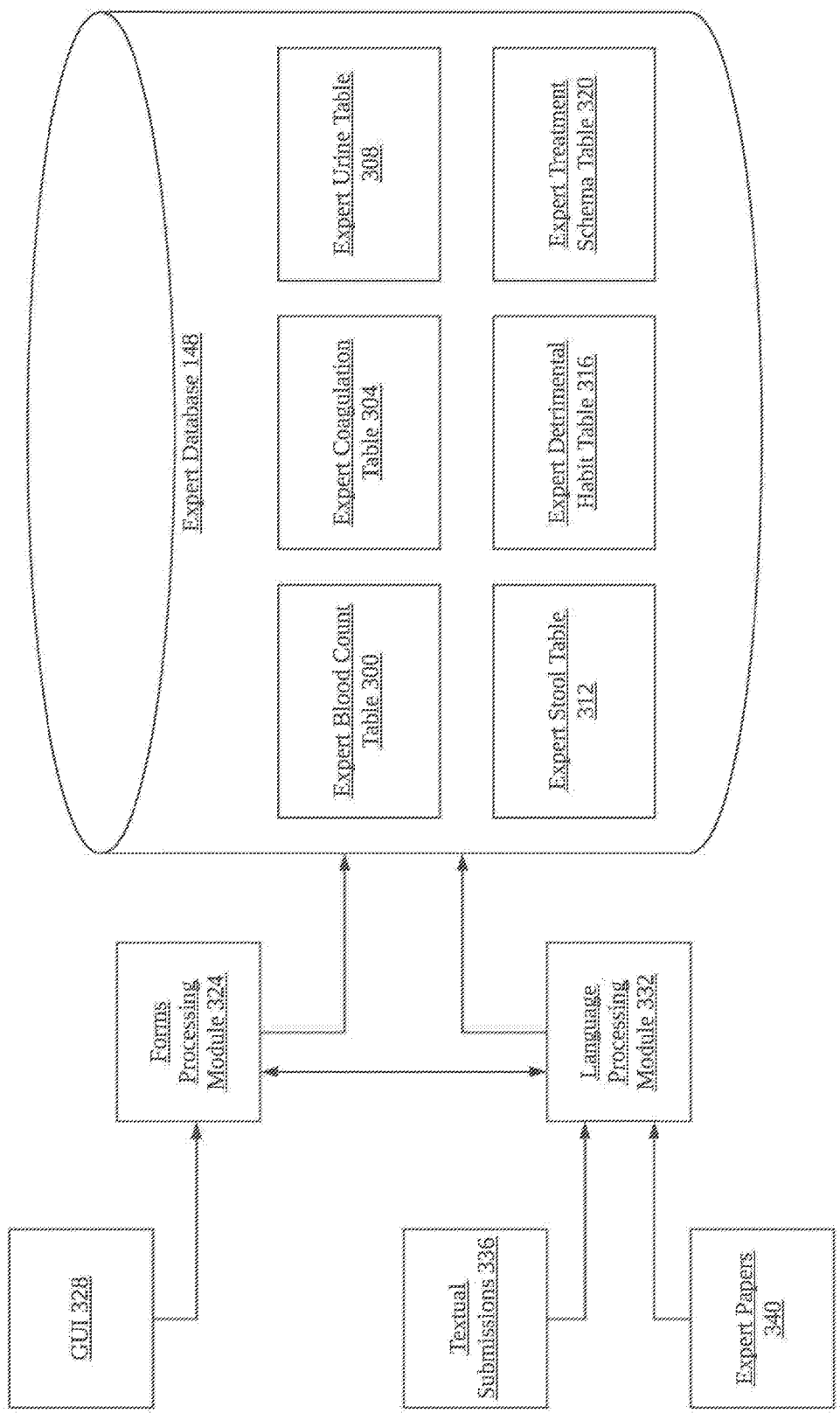
FIG. 3 is a block diagram illustrating an exemplary embodiment of an expert database.

Still referring to FIG. 1, at least a first computing device 104 may detect further significant categories of physiological state data, relationships of such categories to remedial process labels, and/or categories of remedial process labels using machine-learning processes, including without limitation unsupervised machine-learning processes as described above; such newly identified categories, as well as categories entered by experts in free-form fields, may be added to pre-populated lists of categories, lists used to identify language elements for language learning module, and/or lists used to identify and/or score categories detected in documents, as described below in reference to FIG. 3.

Still referring to FIG. 1, ranked remedial attribute lists 140 may be transmitted by at least a first computing device 104 to at least a second computing device 112 as a function of the ranked plurality of remedial attribute list 140 entries. For example, ranked remedial attribute lists 140 may be transferred to the mobile device of a patient, where remedial process labels (or proposed treatments) based on the at least a user constitutional datum 108 and/or at least a user ailment state 120 are presented in order of determined significance that may help the patient get to a constitutionally state more quickly. User may enter a user command to modify or replace one or more parameters and/or attributes of ranked remedial attribute list 140, for example patient may indicate they have no interest in a certain proposed treatment. At least a first computing device 104 may then receive the user command modifying the ranked remedial attribute list 140, wherein a remedial attribute list 140 is derived using the ranked remedial attribute list 140 and the user command, for example to exclude a proposed treatment for a patient or include an additional non-proposed treatment. In an embodiment, presenting a ranked remedial attribute list 140 to a patient gives the patient an opportunity to view a plurality of possible treatment options in order of treatments calculated to have the most to least effect on getting such patient back to a constitutionally state, and allowing such patient to indicate any treatment options they wish to exclude and/or include based on the recommendations presented to them.

With continued reference to FIG. 1, deriving the remedial attribute list 140 by the at least a first computing device 104 may include generating a default attribute listing, transmitting the default attribute listing to the user, receiving a user command modifying the default attribute listing, and deriving the remedial attribute list 140 using the default attribute listing and the user command. Generating the default attribute listing herein may further include receiving a training set correlating a collection of individual information to individual remedial attribute lists 140, generating a set of user data regarding the user, and deriving the default attribute listing from the training set as a function of the set of user data using a K-nearest neighbors algorithm. Deriving the user remedial attribute list 140 may include generating a default attribute listing wherein a default attribute listing may contain default values that represent a "first guess" by system 100 for what user's relative priorities are likely to be; values herein may relate to a default at least a user willingness datum. Default attribute listing may be stored in and/or retrieved from expert database 152, which may be populated based on an expert determination of likely priorities. Alternatively, a person acquainted with user may enter, in a display as described above, what that person believes user's priorities are likely to be; multiple such entries may be aggregated, averaged, or the like. In an embodiment, at least a first computing device 104 may use a machine-learning process to generate a default attribute listing; this may be performed by predicting a user's likely priorities and/or preferences based on previously determined priorities and/or preferences of another person. For instance, generating a default attribute listing may include receiving a default attribute listing training set correlating a collection of individual information to individual remedial attribute lists 140. Default attribute listing training set may include a plurality of entries, each entry corresponding to a different person; entries may be anonymized to preserve individual privacy. Each entry of plurality of entries may include a set of personal data, pertaining to a person represented by the entry, which may include any information suitable for inclusion in user database 148 as described below, including user preferences, habits, constitutional information including without limitation blood test, urine tests, stool tests, genetic tests, and the like, user detrimental habit data, user demographic data, and the like. Each entry may also include a user remedial attribute list 140, which may include any element and/or elements suitable for inclusion in user remedial attribute list 140 as described above.

Still referring to FIG. 1, at least a first computing device 104 may generate a set of user data regarding the user; set of user data may be generated to match categories of data in entries in default attribute listing training set. In an embodiment, set of user data may be generated by querying user database 148. Alternatively or additionally, one or more elements of set of user data may be obtained by prompting user to enter the one or more elements at a user device and receiving the one or more elements in response to the prompting; one or more elements may be obtained, alternatively or additionally, by prompting another person, for instance at or via an at least a second computing device 112, to provide the one or more elements of data, and receiving the one or more elements in response. The above-described methods may be combined; for instance, at least a first computing device 104 may query user database 148 to obtain some elements of user data, determine that one or more elements matching categories in default attribute listing database are missing, and prompt user and/or another person to provide such elements. Persons skilled in the art, upon reviewing the entirety of this disclosure, will be aware of various ways in which user data may be collected and/or generated consistently with this disclosure.

With continued reference to FIG. 1, at least a first computing device 104 may derive default attribute listing from training set as a function of set of user data, using any suitable machine learning algorithm. As a non-limiting example, at least a first computing device 104 may derive default attribute listing from training set using a lazy-learning process, which may be a K-nearest neighbors algorithm; K-nearest neighbors may return a single matching entry, or a plurality of matching entries. Where a plurality of matching entries are returned, at least a first computing device 104 may derive default attribute listing from plurality of matching entries by aggregating user remedial attribute list 140 of matching entries; aggregation may be performed using any suitable method for aggregation, including component-wise addition followed by normalization, component-wise calculation of arithmetic means, or the like. Persons skilled in the art, upon reviewing the entirety of this disclosure, will be aware of various ways in which multiple user remedial attribute list 140 may be combined to create a default attribute listing.

Still referring to FIG. 1, deriving the user remedial attribute list 140 may additionally include transmitting a default attribute listing to the user. Default attribute listing may then be displayed to user via at least a second computing device 112. In an embodiment, display of default attribute listing to user may be performed by populating data entry fields usable for user to enter values of remedial attribute list 140 with values taken from default attribute listing. Such populated data entry fields may be displayed to user, indicating a first guess at user's likely preferences. At least a first computing device 104 may receive a user command modifying the default attribute listing; command may be received in the form of a modification and/or replacement by user of a value displayed in a user entry field. At least a first computing device 104 may derive user remedial attribute list 140 using the default attribute listing and the user command; for instance, and without limitation, system may adopt user modifications to default attribute listing to produce a user remedial attribute list 140.

Still referring to FIG. 1, user remedial attribute list 140 may be stored in memory of at least a first computing device 104, including without limitation in user database 148 as described above. User remedial attribute list 140 may be updated periodically; for instance a user may modify user remedial attribute list 140 via a user interface, for instance to change one or more relative priorities to match user remedial attribute list 140. User may enter a command to view user remedial attribute list 140, modify one or more parameters and/or attributes of user remedial attribute list 140, and cause at least a first computing device 104 to store modified at least a user remedial attribute list 140.

Continuing to refer to FIG. 1, at least a first computing device 104 is designed and configured to generate a plurality of treatment schemas 156, where each treatment schema 156 of the plurality of treatment schemas 156 includes a treatment schema attribute listing having a plurality of treatment schema attribute listing entries, the plurality of treatment schema attribute listing entries includes an attribute listing entry corresponding to each remedial attribute list 140 entry of the plurality of remedial attribute list 140 entries, and each treatment schema attribute listing entry indicates a degree of impact on a factor represented by a remedial attribute list 140 entry; such that large numbers in an attribute listing field are associated with treatments having the most success in recovery from an ailment, and those with lower numbers in an attribute listing field associated with treatments having the rates of recovery from an ailment lower than that of those with higher numbers. In an embodiment, degree of impact may be determined by a supervised machine-learning process, as described above, that uses training data associating at least a user constitutional datum 108 of at least a user ailment state 120 and/or at least a remedial process label 128 to variances between actuarial life expectancy datum and actual mortality dates. A "treatment schema" as used in this disclosure is a data element including a set of data elements, called "treatment schema elements," representing actions a user can take that, taken together, probably will lessen negative constitutional impacts related to at least a user constitutional datum 108 that may be harmful and/or at least a user ailment state 120, and thus reduce effective age, where probability is determined by a process as described herein for predicting that a treatment schema 156 will reduce effective age. Attributes of treatment schemas 156 are extracted from the remedial attribute list 140 entries. Each such treatment schema 156 element may be stored in a treatment schema element database 160, which may be implemented in any manner suitable for implementation of user database 148 as described herein.

Continuing to refer to FIG. 1, at least a first computing device 104 may generate each treatment schema 156 of plurality of treatment schemas 156 by combining treatment schema 156 elements, which may be retrieved from treatment schema element database 160. Treatment schema 156 elements for combinations may be selected according to treatment schema 156 elements likely to improve a particular user's state of constitutional, such as reversing detrimental effects to a user's constitutional indicated by any at least a user constitutional datum 108 and/or at least a user ailment state 120; such elements may be identified, without limitation, using expert inputs; for instance expert inputs may link particular at least a user constitutional datum 108 levels and/or change in at least a user constitutional datum 108 levels to particular nutritional goals, exercise goals, sleep goals, or cessation of bad habits, which may in turn be used to retrieve particular treatment schema 156 elements from treatment schema element database 160. Goals extracted from treatment schema element database 160 may align with at least a user willingness level value specifying preferences/priority as described above. As another non-limiting example, one or more expert inputs may identify reductions in bad habits that may improve user life expectancy, one or more programs that may aid in cessation of one or more bad habits, or the like. One or more expert inputs may propose one or more combinations of treatment schema 156 elements that an expert may claim are especially useful, and/or that an expert may have viewed in the past as efficacious or convenient.

With continued reference to FIG. 1, treatment schema 156 element combinations may be selected using machine learning processes. For instance, a treatment schema 156 training set including a plurality of entries may be received, each entry including a profile of a person having given at least a user constitutional datum 108, at least a user ailment state 120, and/or detrimental habits, a treatment schema 156 engaged in by that person, and effect of the treatment schema 156 on a life expectancy of that person; treatment schema 156 training set may be limited to collections of persons sharing a specific at least a user constitutional datum 108 with user, persons sharing a chronological age with user, and/or persons sharing an effective age with user. A machine-learning process may identify persons having the greatest similarity to user, where similarity is matched according to at least a user constitutional datum 108, at least a user ailment state 120, and/or detrimental habits, combined with a life-expectancy improvement goal from remedial attribute list 140. A list of treatment schemas 156 may be selected using a K-nearest neighbors algorithm, a classifier, a lazy-learning algorithm, or a "best match" algorithm. Alternatively or additionally, a treatment schema 156 or treatment schema 156 component may be generated and/or selected by submitting any blood test data, genetic data, measure of endocrine function, genomic test, urine test, or the like to a diagnostic engine configured to generate "ameliorative process labels," defined as labels describing one or more forms of actions that may tend to improve conditions and/or potential future conditions of a person, receiving, from the diagnostic engine, at least an ameliorative process label, and generating and/or selecting a treatment schema 156 and/or treatment schema 156 component as a function of the at least an ameliorative process label; such a diagnostic engine may be implemented, without limitation, as disclosed in U.S. Nonprovisional patent application Ser. No. 16/354,119, filed on Mar. 14, 2019, and entitled ARTIFICIAL INTELLIGENCE SYSTEMS AND METHODS FOR VIBRANT CONSTITUTIONAL GUIDANCE, the entirety of which is incorporated by reference herein.

With continued reference to FIG. 1, each treatment schema 156 of the plurality of treatment schemas 156 includes a treatment schema attribute listing including a plurality of treatment schema attribute listing entries; treatment schema attribute listing, in any given embodiment, may have entries corresponding to entries in remedial attribute list 140. For instance, and without limitation, each treatment schema 156 element may have an associated attribute listing, which may be chosen as a subset of attributes of treatment schema 156 element listed in a database, where each attribute indicates an effect each treatment schema 156 element has on an attribute in remedial attribute list 140; for example, a particular treatment schema 156 element may have a large impact on life expectancy, represented by a large number in an attribute field associated with change to life expectancy, a low cost, represented by a small number in a field associated with cost, and require a large weekly time commitment, indicated by a large number in a field associated with weekly time commitment. Attribute listings associated with treatment schema 156 elements may be stored in treatment schema element database 160 and linked to particular treatment schema 156 elements; these attribute listings may, without limitation, be populated by expert inputs, aggregated user ratings, or the like. At least a first computing device 104 may generate an attribute listing of each treatment schema 156 of plurality of treatment schemas 156 by combining treatment schema 156 elements, for instance via component-wise and/or attribute-wise addition; each treatment schemas 156 attribute listing may then be scaled and/or normalized as described above. As a result, each treatment schema attribute listing entry may indicate a degree of relative impact on a factor represented by a remedial attribute list 140 entry resulting from the treatment schema 156.

Still referring to FIG. 1, at least a first computing device 104 is designed and configured to select a treatment schema 156 from the plurality of treatment schemas 156, where selecting the treatment schema 156 includes generating a loss function of the plurality of treatment schemas 156 and the remedial attribute list 140, minimizing the loss function, and selecting the treatment schema 156 from the plurality of treatment schemas 156 as a function of minimizing the loss function. In an embodiment, selecting the treatment schema 156 further includes generating a loss function of the plurality of treatment schemas 156 and the remedial attribute list 140, minimizing the loss function, and selecting a treatment schema 156 from the plurality of treatment schemas 156 as a function of minimizing the loss function. A "loss function", as used herein is an expression of an output of which an optimization algorithm minimizes to generate an optimal result. As a non-limiting example, at least a first computing device 104 may select a treatment schema 156 having an associated vector that minimizes a measure of difference from remedial attribute list 140; measure of difference may include, without limitation, a measure of geometric divergence between treatment schema attribute listing and remedial attribute list 140, such as without limitation cosine similarity, or may include any suitable error function measuring any degree of divergence and/or aggregation of degrees of divergence, between attributes of user remedial attribute list 140 and treatment schema attribute listings. Selection of different loss functions may result in identification of different treatment schemas 156 as generating minimal outputs. Alternatively or additionally, each of remedial attribute list 140 and each treatment schema attribute listing may be represented by a mathematical expression having the same form as mathematical expression; at least a first computing device 104 may compare the former to the latter using an error function representing average difference between the two mathematical expressions. Error function may, as a non-limiting example, be calculated using the average difference between coefficients corresponding to each variable. A treatment schema 156 having a mathematical expression minimizing the error function may be selected, as representing an optimal expression of relative importance of variables to a system or user. In an embodiment, error function and loss function calculations may be combined; for instance, a variable resulting in a minimal aggregate expression of error function and loss function, such as a simple addition, arithmetic mean, or the like of the error function with the loss function, may be selected, corresponding to an option that minimizes total variance from optimal variables while simultaneously minimizing a degree of variance from a set of priorities corresponding to variables. Coefficients of mathematical expression and/or loss function may be scaled and/or normalized; this may permit comparison and/or error function calculation to be performed without skewing by varied absolute quantities of numbers. At least a first computing device 104 may select a plurality of treatment schemas 156 to user; for instance, ranking may be maintained of treatment schemas 156 according to a degree to which they minimize loss function, and a number of highest-ranking treatment schemas 156, such as the ten highest ranking treatment schemas 156 or the like, may be selected.

Continuing to refer to FIG. 1, at least a first computing device 104 is designed and configured to transmit the selected treatment schema 156 to at least a second computing device 112. At least a first computing device 104 may be configured to transmit and present selected treatment schema 156 and/or treatment schemas 156 to user; for instance, treatment schema attribute listing of each selected treatment schema 156 may be presented. This may, in an embodiment, have the result that the user is able to see an impact on life expectancy of a given treatment schema 156, as well as its impact on one or more additional willingness priorities that user has specified in remedial attribute list 140. At least a first computing device 104 may additionally select a treatment schema 156 maximizing impact on life expectancy, for instance by running loss function against an attribute listing having all elements except life expectancy impact set to zero; this may be displayed as well to inform the user of a maximal possible impact on life expectancy. In an embodiment, at least a first computing device 104 may receive user input modifying remedial attribute list 140, for instance as described above; at least a first computing device 104 may repeat above-described processes for selection of one or more treatment schemas 156, including any cost-function process, and display selected treatment schemas 156 a second time.

With continued reference to FIG. 1, transmitting the selected treatment schema 156 by the at least a first computing device 104 may include assigning significance scores to the plurality of treatment schemas 156, ranking the plurality of treatment schemas 156 as a function of the significance scores, and transmitting the selected treatment schema 156 with the ranked plurality of treatment schemas 156. Assigning of significance scores and ranking based on significance scores of the plurality of treatment schemas 156 may be performed as described above for a plurality of remedial attribute list 140 entries. In an embodiment, user may be presented with a singular best treatment schema 156 coinciding with information from, for example, at least a user willingness level, expert opinions, and the like as mentioned throughout this disclosure; or such plurality of treatment schemas 156 may be presented to a user ranked in order of significance scores, allowing the user to assess a multitude of treatment schema 156 options.

With continued reference to FIG. 1, transmitting the selected treatment schema 156 by the at least a first computing device 104 may include extracting, from an expert knowledge database, best practices for treatment of the at least a user ailment state 120, and transmitting the selected treatment schema 156 with the best practices for treatment. Expert knowledge database, as described in more detail below, may contain best practices for treating at least a user constitutional datum 108 that may be detrimental and/or at least a user ailment state 120. Best practice treatment schemas 156, such as best practices in constitutionalcare, may identify the best diagnostic, treatment and preventive techniques, focusing on specific populations of patients and a wide variety of diagnoses and procedures, for addressing heart care, emergency medicine, cancer, orthopedics, childbirth, pulmonary disease and multitudes of other medical conditions; all of which may be present in expert database 152 as individual entries by experts, as published scientific papers, and/or other documents or descriptions of purposes. Best practices for treating specific at least a user constitutional datum 108 and/or at least a user ailment state 120 may be presented along with the selected treatment schema 156 to user regardless of other factors such as user willingness level for user assessment of what is regarded as having the best therapeutic advantage for a user condition; though the selected treatment schema 156 may be that which is regarded as the best practice. For example, best practices for treating diabetes type 2 may include early and aggressive control of glycemia, dyslipidemia, and blood pressure, combined with adoption of common elements endorsed by the chronic heart care model including team care, improved information technology, clinical decision support, self-management education, and delivery system redesign, such treatment requiring a certain time commitment from a patient/user for maximum therapeutic effect, but which may be limited by a user if at least a user willingness level indicates one cannot commit the time to all facets of this treatment.

With continued reference to FIG. 1, the at least a first computing device 104 of system 100 may include receiving, from at least a second computing device 112, a user command modifying the remedial attribute list 140 of the selected treatment schema 156, deriving an updated remedial attribute list 140, where the updated remedial attribute list 140 further including a plurality of remedial attribute list 140 entries, generating a plurality of updated treatment schemas 156, selecting an updated treatment schema 156 from the plurality of updated treatment schemas 156, and transmitting the selected updated treatment schema 156 to at least a second computing device 112. In an embodiment, a user command may be influenced by a loved one or close friend who may have an impact part of treatment decision making process. In an embodiment, at least a user constitutional datum 108, at least a user ailment state 120, detrimental habit, or any other factor impacting individual constitutional may change over time and an originally selected treatment schema 156 may need to be modified. For example, user or constitutionalcare professional can modify with user commands the remedial attribute list 140 of such selected treatment schema 156, where an updated remedial attribute list 140 is then derived, a plurality of updated treatment schemas 156 are generated, an updated treatment schema 156 is selected, and the updated treatment schema 156 is transmitted to at least a second computing device 112; a process that may be achieved in a manner as described above from processing such data from a remedial attribute list 140 to a selected/transmitted treatment schema 156.

Figure 2:
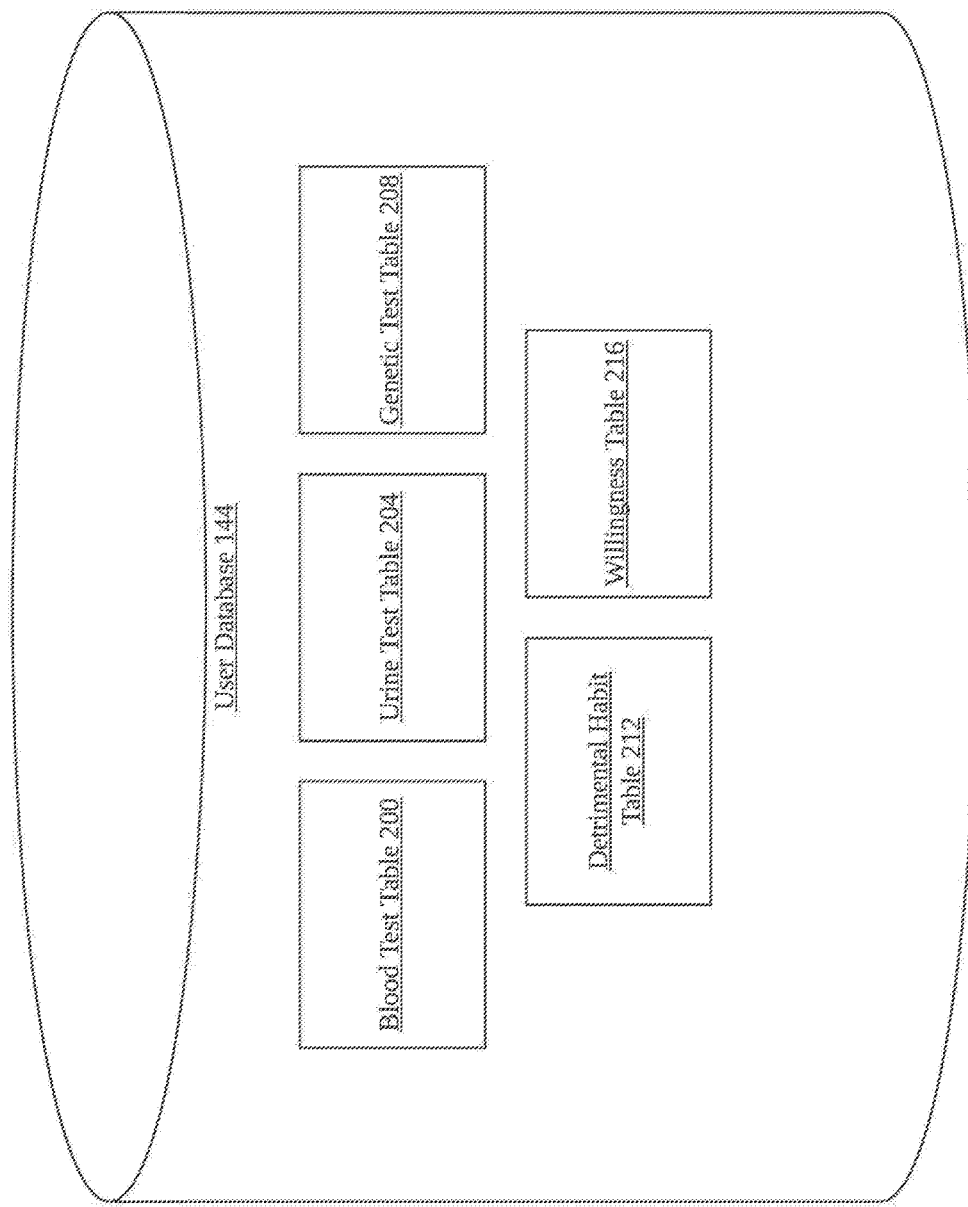
FIG. 2 is a block diagram illustrating an exemplary embodiment of a user database.

Now referring to FIG. 2, an exemplary embodiment of a user database 148 is illustrated. One or more database tables in user database 148 may include, as a non-limiting example, a blood test table 200, which may record data received by at least a first computing device 104 regarding a user blood test as described above. One or more database tables in user database 148 may include, as a non-limiting example, a urine test table 204, which may record data received by at least a first computing device 104 regarding at least a measure of user urine levels, such as for example pH value, protein, glucose, nitrite, ketone, bilirubin, urobilinogen, red blood cell, white blood cell, creatinine, bacteria, casts, crystals, and epithelial cell levels, and the like. One or more database tables in user database 148 may include, as a non-limiting example, a genetic test table 208, which may record data received by at least a first computing device 104 regarding at least a measure of genetic/genomic/transcriptomic/proteomic indices as described above. One or more database tables in user database 148 may include, as a non-limiting example, detrimental habit table 212, which may record data received by at least a first computing device 104 regarding a user detrimental habit as described above. User detrimental habit may be identified by a user entry; for instance, and without limitation, at least a first computing device 104 may provide a user with a questionnaire in the form of one or more data fields requesting that the user identify activities in which the user engaged. Questions presented to a user may include a number of servings of alcohol a user consumes during a given period of time such as a day, a week or a year, a quantity of tobacco, drugs, or other substances that a user consumes during a given period of time, a number of hours a user sleeps in a night, or the like. A user may respond to such questions by selecting options corresponding to particular ranges of data, by setting sliders or other indicators of a quantity along a continuous range, by entering values in drop-down lists, and/or by typing in numbers or text. One or more database tables in user database 148 may include, as a non-limiting example, willingness table 216, which may record data received by at least a first computing device 104 regarding a user willingness levels as described above.

Referring now to FIG. 3, an exemplary embodiment of an expert database 152 is illustrated. Expert database 152 may, as a non-limiting example, organize data stored in the expert database 152 according to one or more database tables. One or more database tables may be linked to one another by, for instance, common column values. For instance, a common column between two tables of expert database 152 may include an identifier of an expert submission, such as a form entry, textual submission, expert paper, or the like, for instance as defined above; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 3, one or more database tables in expert database 152 may include, as a non-limiting example, an expert blood count table 300. Expert blood count table 300 may include any information provided by one or more experts regarding at least a measure of red and white blood cell counts, morphologies, and pathologies, user age factor, and/or other expert data regarding red and while blood cell information as described in this disclosure. Further examples may include expert submission on any tests related to red blood cells such as a complete blood count, and diseases related to red blood cells such as anemia, polycythemia, alpha-thalassemia, beta-thalassemia, kidney disease, vitamin B12 deficiency, or any other of a multitude of diseases affecting red blood cells. Further examples may include any tests related to red blood cells such as a complete blood count, and diseases related to white blood cells such as leukocytosis (i.e. bacterial and viral infections, fungal infections, parasitic infections; inflammatory diseases such as rheumatoid arthritis or inflammatory bowel disease; leukemia, trauma causing tissue death, allergic reactions, or numerous others), leukopenia (i.e. bone marrow damage and disorders, folate and B12 deficiencies, lymphoma, autoimmune disorders, sepsis, HIV, or numerous others), or the like which affect aspects of white blood cells. One or more database tables in expert database 152 may include, as a non-limiting example, an expert coagulation table 304. Expert coagulation table 304 may include any information provided by one or more experts regarding user platelet coagulation information as described in this disclosure. Examples may include expert submission on any tests related to platelet coagulation such as prothrombin time, partial thromboplastin time, fibrinogen, or the like, and disorders affecting or relating to coagulation such as, for example, idiopathic thrombocytopenic purpura, chronic myelogenous leukemia, multiple myeloma, myelofibrosis, thrombocythemia, and numerous others. One or more database tables in expert database 152 may include, as a non-limiting example, an expert urine table 308. Expert urine table 308 may include any information provided by one or more experts regarding tests and disorders related to urine levels as described previously. One or more database tables in expert database 152 may include, as a non-limiting example, an expert stool table 312. Expert stool table 312 may include any information provided by one or more experts regarding tests and disorders related to stool levels as described above, including those of the microbiome and gut disorders. One or more database tables in expert database 152 may include, as a non-limiting example, an expert detrimental habit table 316. Expert detrimental habit table 316 may include any information provided by one or more experts regarding user detrimental habits, user detrimental habit factor, and/or other expert data regarding detrimental habit related information as described in this disclosure. One or more database tables in expert database 152 may include, as a non-limiting example, an expert treatment schema 156 table 320. Expert treatment schema 156 table 320 may include any information provided by one or more experts regarding treatment schemas 156, treatment schema 156 elements, and/or attribute listings associated therewith, as described in further detail above.

In an embodiment, and still referring to FIG. 3, a forms processing module 324 may sort data entered in a submission via a graphical user interface (GUI) 328 receiving expert submissions by, for instance, sorting data from entries in the graphical user interface 328 to related categories of data; for instance, data entered in an entry relating in the graphical user interface 328 to at least a user constitutional datum 108 and/or at least a user ailment state 120 may be sorted into variables and/or data structures for blood count, which may be provided to expert blood count table 300 300, while data entered in an entry relating to coagulation may be sorted into variables and/or data structures for the storage of platelet coagulation such as expert coagulation table 304, while data entered in an entry relating to urine may be sorted into variables and/or data structures for the storage of urine-related data such as expert urine table 308, while data entered in an entry relating to stool may be sorted into variables and/or data structures for the storage of stool-related data such as expert stool table 312. Where data is chosen by an expert from pre-selected entries such as drop-down lists, data may be stored directly; where data is entered in textual form, a language processing module 332 may be used to map data to an appropriate existing label, for instance using an attribute listing similarity test or other synonym-sensitive language processing test to map data to existing labels and/or categories. Similarly, data from an expert textual submissions 336, such as accomplished by filling out a paper or PDF form and/or submitting narrative information, may likewise be processed using language processing module.

Still referring to FIG. 3, a language processing module 332 may include any hardware and/or software module. Language processing module 332 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 1, language processing module 332 may compare extracted words to categories of data to be analyzed; such data for comparison may be entered on at least a first computing device 104 as described above using expert data inputs or the like. In an embodiment, one or more categories may be enumerated, to find total count of mentions in such documents. Alternatively or additionally, language processing module 332 may operate to produce a language processing model. Language processing model may include a program automatically generated by at least a server and/or language processing module 332 to produce associations between one or more words extracted from at least a document and detect associations, including without limitation mathematical associations, between such words, and/or associations between such words and other elements of data analyzed, processed and/or stored by system 100. Associations between language elements, may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of physiological data, a given relationship of such categories to remedial process labels, and/or a given category of remedial process labels. As a further example, statistical correlations and/or mathematical associations may include probabilistic formulas or relationships indicating a positive and/or negative association between at least an extracted word and/or a given category of data; positive or negative indication may include an indication that a given document is or is not indicating a category of data.

Still referring to FIG. 3, language processing module 332 and/or at least a first computing device 104 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs, as used herein, are statistical models with inference algorithms that that may be applied to the models. In such models, a hidden state to be estimated may include an association between an extracted word category of physiological data, a given relationship of such categories to remedial process labels, and/or a given category of remedial process labels. There may be a finite number of category of physiological data, a given relationship of such categories to remedial process labels, and/or a given category of remedial process labels to which an extracted word may pertain; an HMM inference algorithm, such as the forward-backward algorithm or the Viterbi algorithm, may be used to estimate the most likely discrete state given a word or sequence of words. Language processing module 324 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model may include generating an attribute listing (i.e. vector) space, which may be a collection of attribute listings, defined as a set of mathematical objects that can be added together under an operation of addition following properties of associativity, commutativity, existence of an identity element, and existence of an inverse element for each attribute listing, and can be multiplied by scalar values under an operation of scalar multiplication compatible with field multiplication, and that has an identity element is distributive with respect to attribute listing addition, and is distributive with respect to field addition. Each attribute listing in an n-dimensional attribute listing space may be represented by an n-tuple of numerical values. Each unique extracted word and/or language element as described above may be represented by an attribute listing of the attribute listing space. In an embodiment, each unique extracted and/or other language element may be represented by a dimension of attribute listing space; as a non-limiting example, each element of an attribute listing may include a number representing an enumeration of co-occurrences of the word and/or language element represented by the attribute listing with another word and/or language element. Attribute listings may be normalized, scaled according to relative frequencies of appearance and/or file sizes. In an embodiment associating language elements to one another as described above may include computing a degree of attribute listing similarity between an attribute listing representing each language element and a attribute listing representing another language element; attribute listing similarity may be measured according to any norm for proximity and/or similarity of two attribute listings, including without limitation cosine similarity, which measures the similarity of two attribute listings by evaluating the cosine of the angle between the attribute listings, which can be computed using a dot product of the two attribute listings divided by the lengths of the two attribute listings. Degree of similarity may include any other geometric measure of distance between attribute listings.

Still referring to FIG. 3, language processing module 332 may use a corpus of documents to generate associations between language elements in a language processing module 332, and at least a first computing device 104 may then use such associations to analyze words extracted from one or more documents. Documents may be entered into classification device by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, classification device may automatically obtain the document using such an identifier, for instance by submitting a request to a database or compendium of documents such as JSTOR as provided by Ithaka Harbors, Inc. of New York.

Data may be extracted from expert papers 340, which may include without limitation publications in medical and/or scientific journals, by language processing module 332 via any suitable process as described herein. Persons skilled in the art, upon reviewing the entirety of this disclosure, will be aware of various additional methods whereby novel terms may be separated from already-classified terms and/or synonyms therefore, as consistent with this disclosure.

Figure 4:
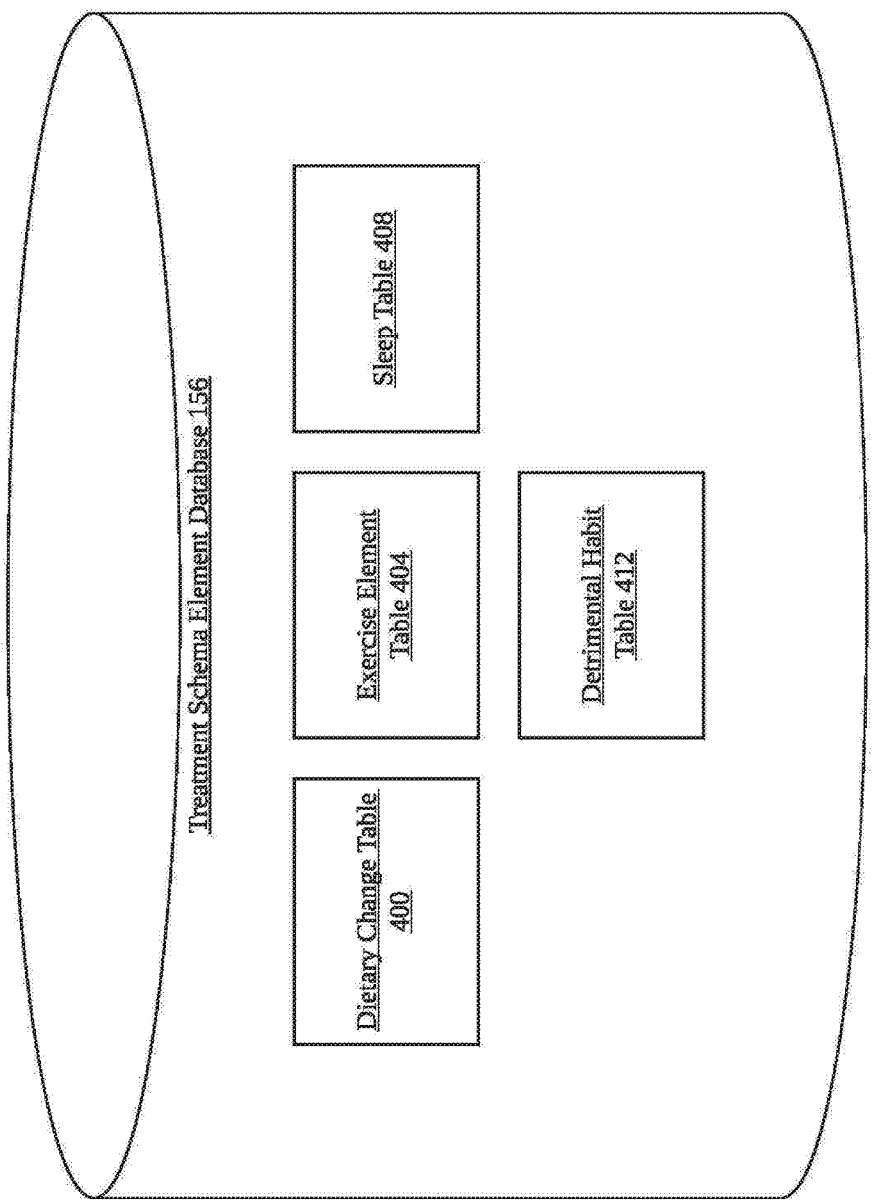
FIG. 4 is a block diagram illustrating an exemplary embodiment of treatment schema element database.

Now referring to FIG. 4, an exemplary embodiment of treatment schema element database 160 is illustrated. Treatment schema element database 160 may include a dietary change table 400, which may contain, without limitation, treatment schema 156 elements corresponding to dietary changes, such as without limitation a reduction in the daily consumption of a particular nutrient, an increase in the daily consumption of a particular nutrient, a decrease in the daily consumption of a given category of food, an increase in the daily consumption of a given category of food, or the like. For instance, and without limitation, a treatment schema 156 element may include cessation of meat consumption, an addition of one serving of fruit per day, a halving of daily saturated fat intake as measured in calories and/or grams of saturated fat, or the like. Treatment schema 156 elements pertaining to nutritional goals may list particular meals, meal plans, food elements, or the like, together with corresponding nutritional goals met by such meals, meal plans, and/or food elements. Treatment schema element database 160 may include an exercise element table 404, which may contain treatment schema 156 elements that include one or more measurable exercise goals, such as a goal to take some target number of steps per day, a goal to burn a target number of calories per day, a goal to engage in a certain amount of cardiovascular exercise at a given intensity level, as represented for instance by a number on a discrete scale from 1 to 10, where 1 is a minimal intensity and 10 is a maximal intensity, a goal to engage in a certain amount of resistance training at a given intensity level, which may be similarly represented, a goal to spend a certain quantity of time per day stretching, or the like. Treatment schema 156 elements pertaining to exercise goals may include particular forms of exercise, such as jogging, biking, weightlifting, or the like, which may list corresponding exercise goals that match the treatment schema 156 elements. Treatment schema element database 160 may include, without limitation, a sleep table 408, which may record one or more treatment schema 156 elements to sleep goals, such as a goal to sleep a certain number of hours per week or per day, to set a fixed bedtime, or the like. Treatment schema 156 element table may include, without limitation, a detrimental habit table 412, which may record information elements relating to a cessation or reduction of a detrimental habit, such as tobacco consumption, alcohol consumption, gambling, drug use, or the like; such treatment schema 156 elements may alternatively or additionally list particular programs and/or protocols for reduction in bad habits, such as 12-step programs or the like.

Figure 5:
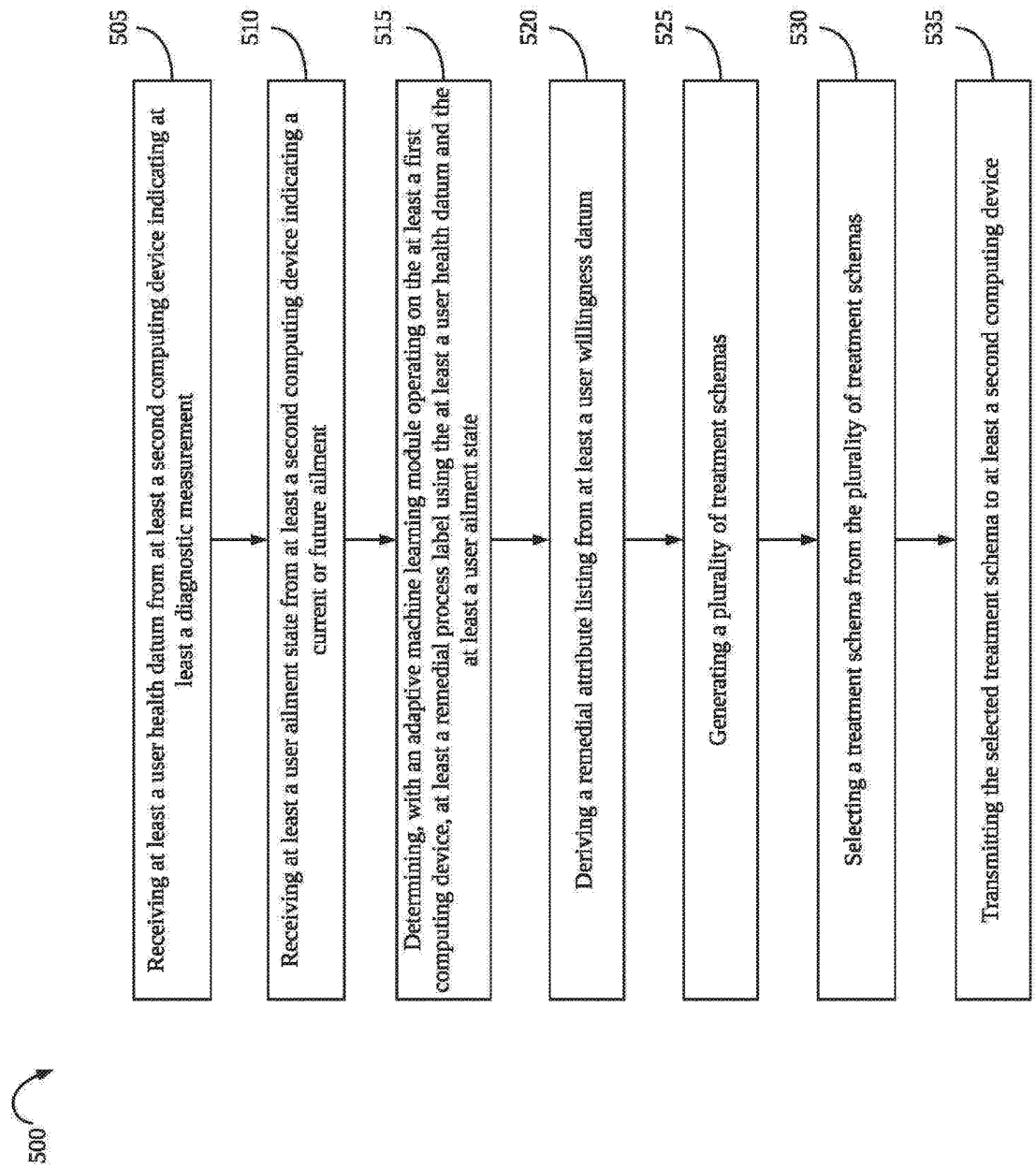
FIG. 5 is a flow diagram illustrating an exemplary embodiment of a method of selecting a treatment schema based on user willingness.

Turning now to FIG. 5, an exemplary embodiment of a method 500 of selecting a treatment schema 156 based on user willingness by at least a first computing device 104 is illustrated. At step 505, at least a first computing device 104 receives at least a user constitutional datum 108 from at least a second computing device 112 indicating at least a diagnostic measurement 116. This may be implemented, without limitation, as described above in reference to FIGS. 1-4. At step 510, the at least a first computing device 104 receives at least a user ailment state 120 from the at least a second computing device 112 indicating a current or future ailment. This may be implemented, without limitation, as described above in reference to FIGS. 1-4. At step 515, the at least a first computing device 104 determines, with an adaptive machine learning module 124 operating on the at least a first computing device 104, at least a remedial process label 128 using the at least a user constitutional datum 108 and the at least a user ailment state 120. This may be implemented, without limitation, as described above in reference to FIGS. 1-4. Determining the at least a remedial process label 128 with the adaptive machine learning module 124 may further include receiving training data correlating at least a user constitutional datum 108 of at least a user ailment state 120 to at least a remedial process label 128, generating, using a supervised machine learning process, a preliminary treatment model 136 that receives at least a user constitutional datum 108 of at least a user ailment state 120 as inputs and produces an output representing the at least a remedial process label 128, and determining the at least a remedial process label 128 using the at least a user constitutional datum 108 of the at least a user ailment state 120 and the preliminary treatment model 136. This method may further include identifying, using an unsupervised machine learning process, a correlation between the at least a user constitutional datum 108 and the at least a user ailment state 120, receiving training data correlating at least a user constitutional datum 108 of at least a user ailment state 120 to at least a remedial process label 128, and generating the training data correlating the at least a user constitutional datum 108 and the at least a user ailment state 120 to the at least a remedial process label 128 using the training data correlating the at least a user constitutional datum 108 of at least a user ailment state 120 and the identified correlation between the at least a user constitutional datum 108 and the at least a user ailment state 120. This may be implemented, without limitation, as described above in reference to FIGS. 1-4. Determining the at least a remedial process label 128 with the adaptive machine learning module 124 may further include receiving training data correlating one or more changes in at least a user constitutional datum 108 of at least a user ailment state 120 to at least a remedial process label 128, generating, using a supervised machine learning process, a preliminary treatment model 136 that receives one or more changes in at least a user constitutional datum 108 of at least a user ailment state 120 as inputs and produces an output representing the at least a remedial process label 128, calculating at least a change in at least a user ailment state 120 using the at least a user constitutional datum 108 of the at least a user ailment state 120, and determining the at least a remedial process label 128 using the at least a change in the at least a user ailment state 120 and the preliminary treatment model 136. This may be implemented, without limitation, as described above in reference to FIGS. 1-4.

At step 520, and still referring to FIG. 5, the at least a first computing device 104 derives a remedial attribute list 140, where the remedial attribute list 140 includes a plurality of remedial attribute list 140 entries including at least a remedial process label 128 value indicating a degree of importance of at least a remedial process, and at least a user willingness level value indicating a numerical measure of a user willingness. This may be implemented, without limitation, as described above in reference to FIGS. 1-4. Deriving the remedial attribute list 140 may further include assigning significance scores to the plurality of remedial attribute list 140 entries, ranking the plurality of remedial attribute list 140 entries as a function of the significance scores, transmitting a ranked remedial attribute list 140 to at least a second computing device 112 as a function of the ranked plurality of remedial attribute list 140 entries, receiving a user command modifying the ranked remedial attribute list 140, and deriving the remedial attribute list 140 using the ranked remedial attribute list 140 and the user command. This may be implemented, without limitation, as described above in reference to FIGS. 1-4. Deriving the remedial attribute list 140 may further include generating a default attribute listing, transmitting the default attribute listing to the user, receiving a user command modifying the default attribute listing, and deriving the remedial attribute list 140 using the default attribute listing and the user command. Generating the default attribute listing may further include receiving a training set correlating a collection of individual information to individual remedial attribute lists 140, generating a set of user data regarding the user, and deriving the default attribute listing from the training set as a function of the set of user data using a K-nearest neighbors algorithm. This may be implemented, without limitation, as described above in reference to FIGS. 1-4.

At step 525, and still referring to FIG. 5, the at least a first computing device 104 generates a plurality of treatment schemas 156, where each treatment schema 156 of the plurality of treatment schemas 156 includes a treatment schema attribute listing having a plurality of treatment schema attribute listing entries, the plurality of treatment schema attribute listing entries includes an attribute listing entry corresponding to each remedial attribute list 140 entry of the plurality of remedial attribute list 140 entries, and each treatment schema attribute listing entry indicates a degree of impact on a factor represented by a remedial attribute list 140 entry. This may be implemented, without limitation, as described above in reference to FIGS. 1-4. At step 530, the at least a first computing device 104 selects a treatment schema 156 from the plurality of treatment schemas 156, where selecting the treatment schema 156 includes generating a loss function of the plurality of treatment schemas 156 and the remedial attribute list 140, minimizing the loss function, and selecting the treatment schema 156 from the plurality of treatment schemas 156 as a function of minimizing the loss function. This may be implemented, without limitation, as described above in reference to FIGS. 1-4.

At step 535, and still referring to FIG. 5, the at least a first computing device 104 transmits the selected treatment schema 156 to at least a second computing device 112. This may be implemented, without limitation, as described above in reference to FIGS. 1-4. Transmitting the selected treatment schema 156 may further include assigning significance scores to the plurality of treatment schemas 156; ranking the plurality of treatment schemas 156 as a function of the significance scores, and transmitting the selected treatment schema 156 with the ranked plurality of treatment schemas 156. This may be implemented, without limitation, as described above in reference to FIGS. 1-4. Transmitting the selected treatment schema 156 may further include extracting, from an expert knowledge database, best practices for treatment of the at least a user ailment state 120, and transmitting the selected treatment schema 156 with the best practices for treatment. This may be implemented, without limitation, as described above in reference to FIGS. 1-4. Method 500 may further include receiving, from at least a second computing device 112, a user command modifying the remedial attribute list 140 of the selected treatment schema 156, deriving an updated remedial attribute list 140, where the updated remedial attribute list 140 further includes a plurality of remedial attribute list 140 entries, generating a plurality of updated treatment schemas 156, selecting an updated treatment schema 156 from the plurality of updated treatment schemas 156, and transmitting the selected updated treatment schema 156 to at least a second computing device 112. A user command modifying the remedial attribute list may be influenced by a loved one or close friend who may have an impactful part of this decision making process.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
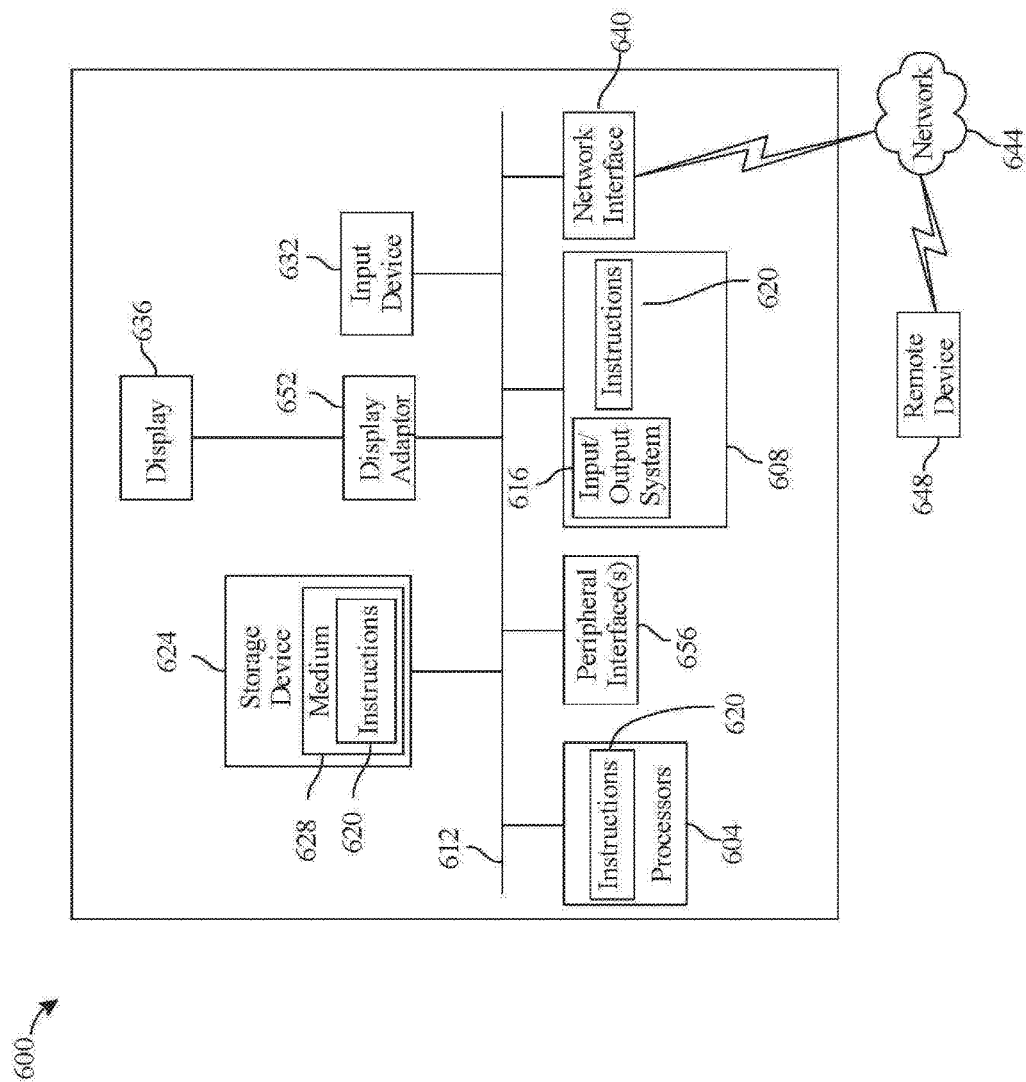
FIG. 6 is a block diagram of a computing system that can be used to implement any one or more of the methodologies disclosed herein and any one or more portions thereof.

FIG. 6 shows a diagrammatic representation of one embodiment of a computing device in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Memory 608 may include various components (e.g., machine-readable media) including, but not limited to, a random access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIRE-WIRE interface, a direct interface to bus 612, and any combinations thereof. Input device 632 may include a touch screen interface that may be a part of or separate from transmit 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video transmit adapter 652 for communicating a transmitable image to a transmit device, such as transmit device 636. Examples of a transmit device include, but are not limited to, a liquid crystal transmit (LCD), a cathode ray tube (CRT), a plasma transmit, a light emitting diode (LED) transmit, and any combinations thereof. Transmit adapter 652 and transmit device 636 may be utilized in combination with processor 604 to provide graphical representations of aspects of the present disclosure. In addition to a transmit device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for selecting a treatment schema based on user willingness, the system comprising at least a first computing device designed and configured to:
   receive at least a user constitutional datum from at least a second computing device indicating at least a medical test measurement of a user and a diagnostic measurement, wherein receiving the at least a user constitutional datum comprises:
       receiving at least one submission from the user;
       generate a plurality of tokens as a function of the at least one submission using a natural language processor; and
       identify the at least a user constitutional datum from the plurality of tokens;
   receive at least a user ailment state from the at least a second computing device indicating a current or future ailment;
   receive a user willingness datum;
   determine, using an adaptive machine learning module, at least a remedial process label using the at least a medical test measurement and the at least a user ailment state, wherein the adaptive machine learning process uses training data correlating the at least a user ailment state and the at least a remedial process label to variances between actuarial life expectancy datum and actual mortality dates, wherein correlations are an output derived based on a degree of impact calculated using a machine leaching model trained with training data correlating input data describing both the at least a user constitutional datum and a plurality of remedial process labels to the user willingness datum;
   derive a ranked remedial attribute list from at least the user willingness datum, wherein the user willingness datum comprises an attribute indicating a degree of importance to the user of a detrimental habit and wherein the ranked remedial attribute list further comprises a plurality of remedial attribute list entries each including:
       a remedial process label value indicating a degree of importance of at least a remedial process label;
       at least a user willingness level value indicating a numerical measure of a user willingness; and
       a remedial process significance score indicating a numerical measure of a diagnostic relevance between the received at least a medical test and a type of physiological state data;
       wherein each remedial attribute list entry of the ranked remedial attribute list is ranked according to a respective remedial process significance score;

transmit the ranked remedial attribute list to the at least a second computing device, said ranked remedial attribute list configured to display, using a graphical user interface, at least a portion of the plurality of remedial attribute list entries to the user on the at least a second computing device;

receive a selection of a remedial attribute list entry displayed on the second computing device from the user by way of the graphical user interface; and modify the ranked remedial attribute list based upon the selection of the remedial attribute list entry to produce a modified remedial attribute list, said modified remedial attribute list comprising a modified plurality of remedial attribute list entries;

generate a plurality of treatment schemas, wherein;
   each treatment schema of the plurality of treatment schemas includes a treatment schema attribute listing having a plurality of treatment schema attribute listing entries;
   the plurality of treatment schema attribute listing entries includes an attribute listing entry corresponding to each modified remedial attribute list entry of the modified plurality of remedial attribute list entries; and
   each treatment schema attribute listing entry indicates a degree of impact on a factor represented by a modified remedial attribute list entry of the plurality of remedial attribute list entries;

select a treatment schema from the plurality of treatment schemas, wherein selecting the treatment schema further comprises:
   generating a loss function of the plurality of treatment schemas and the modified remedial attribute list;
   minimizing the loss function; and
   selecting the treatment schema from the plurality of treatment schemas as a function of minimizing the loss function;

determine a second treatment schema which maximizes impact on life expectancy of the user by minimizing the loss function based on all treatment schema attribute listing entries except life expectancy impact set to zero; and transmit the selected treatment schema and the second treatment schema to the at least a second computing device.

2. The system of claim 1, wherein determining the at least a remedial process label with the adaptive machine learning module further comprises:
   receiving training data correlating at least a user constitutional datum of at least a user ailment state to at least a remedial process label;
   generating, using a supervised machine learning process, a preliminary treatment model that receives the training data of the at least a user constitutional datum of the at least a user ailment state as inputs and produces an output representing the at least a remedial process label; and
   determining the at least a remedial process label using the at least a user constitutional datum of the at least a user ailment state and the preliminary treatment model.

3. The system of claim 2 further comprising:
   identifying, using an unsupervised machine learning process, a correlation between the at least a user constitutional datum and the at least a user ailment state;
   receiving training data correlating at least a user constitutional datum of at least a user ailment state to at least a remedial process label; and
   generating the training data correlating the at least a user constitutional datum of the at least a user ailment state to the at least a remedial process label using the training data correlating the at least a user constitutional datum of at least a user ailment state and the identified correlation between the at least a user constitutional datum and the at least a user ailment state.

4. The system of claim 1, wherein determining the at least a remedial process label with the adaptive machine learning module further comprises:
   receiving training data correlating one or more changes in at least a user constitutional datum of at least a user ailment state to at least a remedial process label;
   generating, using a supervised machine learning process, a preliminary treatment model that receives the one or more changes in the at least a user constitutional datum of the at least a user ailment state as inputs and produces an output representing the at least a remedial process label;
   calculating at least a change in at least a user ailment state using the at least a user constitutional datum of the at least a user ailment state; and
   determining the at least a remedial process label using the at least a change in the at least a user ailment state and the preliminary treatment model.

5. The system of claim 1, wherein deriving the ranked remedial attribute list further comprises:
   assigning significance scores to the plurality of remedial attribute list entries; and
   ranking the plurality of remedial attribute list entries as a function of the significance scores.

6. The system of claim 1, wherein deriving the ranked remedial attribute list further comprises:
   generating a default attribute listing;
   transmitting the default attribute listing to the user;
   receiving a user command modifying the default attribute listing; and
   deriving the ranked remedial attribute list using the default attribute listing and the user command.

7. The system of claim 6, wherein generating the default attribute listing further comprises:
   receiving a training set correlating a collection of individual information to individual remedial attribute lists;
   generating a set of user data regarding the user; and
   deriving the default attribute listing from the training set as a function of the set of user data using a K-nearest neighbors algorithm.

8. The system of claim 1, wherein transmitting the selected treatment schema further comprises:
   assigning significance scores to the plurality of treatment schemas;
   ranking the plurality of treatment schemas as a function of the significance scores; and
   transmitting the selected treatment schema with the ranked plurality of treatment schemas.

9. The system of claim 1, wherein transmitting the selected treatment schema further comprises:
   extracting, from an expert knowledge database, best practices for treatment of the at least a user ailment state; and
   transmitting the selected treatment schema with the best practices for treatment.

10. A method of selecting a treatment schema based on user willingness by at least a first computing device, the method comprising:
   receiving at least a user constitutional datum from at least a second computing device indicating at least a medical test measurement of a user and a diagnostic measurement, wherein receiving the at least a user constitutional datum comprises:
  receiving at least one submission from the user;
  generate a plurality of tokens as a function of the at least one submission using a natural language processor; and
  identify the user constitutional datum from the plurality of tokens;
wherein the diagnostic measurement includes a signal from at least a sensor configured to detect physiological data of the user and record the diagnostic measurement as a function of the signal, wherein the at least a second computing device is associated with the user and comprises a graphical user interface;
receiving at least a user ailment state from the at least a second computing device indicating a current or future ailment;
receiving a user willingness datum;
determining, with an adaptive machine learning module operating on the at least a first computing device, at least a remedial process label using the at least a medical test measurement and the at least a user ailment state, wherein the adaptive machine learning module uses training data correlating the at least a user ailment state and the at least a remedial process label to variances between actuarial life expectancy datum and actual mortality dates, wherein correlations are an output derived based on a degree of impact calculated using a machine leaching model trained with training data correlating input data describing both the at least a user constitutional datum and a plurality of remedial process labels to the user willingness datum;
deriving a ranked remedial attribute list from at least a user willingness datum, wherein the user willingness datum comprises an attribute indicating a degree of importance to the user of a detrimental habit and wherein the ranked remedial attribute list further comprises a plurality of remedial attribute list entries each including:
  a remedial process label value indicating a degree of importance of at least a remedial process label;
  at least a user willingness level value indicating a numerical measure of a user willingness; and
  a remedial process significance score indicating a numerical measure of a diagnostic relevance between the received at least a medical test and a type of physiological state data;
  wherein each remedial attribute list entry of the ranked remedial attribute list is ranked according to a respective remedial process significance score;
transmitting the ranked remedial attribute list to the at least a second computing device, said ranked remedial attribute list configured to display, using the graphical user interface, at least a portion of the plurality of remedial attribute list entries to the user on the at least a second computing device from the user by way of the graphical user interface;
receiving a selection of a remedial attribute list entry displayed on the second computing device; and
modifying the ranked remedial attribute list based upon the selection of the remedial attribute list entry to produce a modified remedial attribute list, said modified remedial attribute list comprising a modified plurality of remedial attribute list entries;
generating a plurality of treatment schemas, wherein;
  each treatment schema of the plurality of treatment schemas includes a treatment schema attribute listing having a plurality of treatment schema attribute listing entries;
  the plurality of treatment schema attribute listing entries includes an attribute listing entry corresponding to each modified remedial attribute list entry of the modified plurality of remedial attribute list entries; and
  each treatment schema attribute listing entry indicates a degree of impact on a factor represented by a modified remedial attribute list entry of the plurality of remedial attribute list entries;
selecting a treatment schema from the plurality of treatment schemas, wherein selecting the treatment schema further comprises:
  generating a loss function of the plurality of treatment schemas and the modified remedial attribute list;
  minimizing the loss function; and
  selecting the treatment schema from the plurality of treatment schemas as a function of minimizing the loss function;
determining a second treatment schema which maximizes impact on life expectancy of the user by minimizing the loss function based on all treatment schema attribute listing entries except life expectancy impact set to zero; and
transmitting the selected treatment schema and the second treatment schema to at the least a second computing device.

11. The method of claim 10, wherein determining the at least a remedial process label with the adaptive machine learning module further comprises:
  receiving training data correlating at least a user constitutional datum of at least a user ailment state to at least a remedial process label;
  generating, using a supervised machine learning process, a preliminary treatment model that receives the training data of the at least a user constitutional datum of the at least a user ailment state as inputs and produces an output representing the at least a remedial process label; and
  determining the at least a remedial process label using the at least a user constitutional datum of the at least a user ailment state and the preliminary treatment model.

12. The method of claim 11 further comprising:
  identifying, using an unsupervised machine learning process, a correlation between the at least a user constitutional datum and the at least a user ailment state;
  receiving training data correlating at least a user constitutional datum of at least a user ailment state to at least a remedial process label; and
  generating the training data correlating the at least a user constitutional datum and the at least a user ailment state to the at least a remedial process label using the training data correlating the at least a user constitutional datum of at least a user ailment state and the identified correlation between the at least a user constitutional datum and the at least a user ailment state.

13. The method of claim 10, wherein determining the at least a remedial process label with the adaptive machine learning module further comprises:
  receiving training data correlating one or more changes in at least a user constitutional datum of at least a user ailment state to at least a remedial process label;
  generating, using a supervised machine learning process, a preliminary treatment model that receives the one or more changes in the at least a user constitutional datum of the at least a user ailment state as inputs and produces an output representing the at least a remedial process label;

calculating at least a change in at least a user ailment state using the at least a user constitutional datum of the at least a user ailment state; and determining the at least a remedial process label using the at least a change in the at least a user ailment state and the preliminary treatment model.

14. The method of claim 10, wherein deriving the ranked remedial attribute list further comprises:

assigning significance scores to the plurality of remedial attribute list entries; and ranking the plurality of remedial attribute list entries as a function of the significance scores.

15. The method of claim 10, wherein deriving the ranked remedial attribute list further comprises:

generating a default attribute listing;

transmitting the default attribute listing to the user;

receiving a user command modifying the default attribute listing; and deriving the ranked remedial attribute list using the default attribute listing and the user command.

16. The method of claim 15, wherein generating the default attribute listing further comprises:

receiving a training set correlating a collection of individual information to individual remedial attribute lists;

generating a set of user data regarding the user; and deriving the default attribute listing from the training set as a function of the set of user data using a K-nearest neighbors algorithm.

17. The method of claim 10, wherein transmitting the selected treatment schema further comprises:

assigning significance scores to the plurality of treatment schemas;

ranking the plurality of treatment schemas as a function of the significance scores; and transmitting the selected treatment schema with the ranked plurality of treatment schemas.

18. The method of claim 10, wherein transmitting the selected treatment schema further comprises:

extracting, from an expert knowledge database, best practices for treatment of the at least a user ailment state; and transmitting the selected treatment schema with the best practices for treatment.

19. A non-transitory machine-readable storage medium containing machine-executable instructions for performing a method of selecting a treatment schema based on user willingness with at least a first computing device, comprising:

a first set of machine-executable instructions for:

receiving at least a user constitutional datum from at least a second computing device indicating at least a medical test-measurement of a user and a diagnostic measurement, wherein receiving the at least a user constitutional datum comprises:

receiving at least one submission from the user;

generate a plurality of tokens as a function of the at least one submission using a natural language processor; and identify the user constitutional datum from the plurality of tokens;

receiving at least a user ailment state from at least a second computing device indicating a current or future ailment;

receiving a user willingness datum;

determining, with adaptive machine learning, at least a remedial process label using the at least a medical test measurement and the at least a user ailment state, wherein the adaptive machine learning module uses training data correlating the at least a user ailment state and the at least a remedial process label to variances between actuarial life expectancy datum and actual mortality dates, wherein correlations are an output derived based on a degree of impact calculated using a machine leaching model trained with training data correlating input data describing both the at least a user constitutional datum and a plurality of remedial process labels to the user willingness datum;

deriving a ranked remedial attribute list from at least a user willingness datum, wherein the user willingness datum comprises an attribute indicating a degree of importance to the user of a detrimental habit and wherein the ranked remedial attribute list further comprises a plurality of remedial attribute list entries each including:

a remedial process label value indicating a degree of importance of at least a remedial process label;

at least a user willingness level value indicating a numerical measure of a user willingness; and a remedial process significance score indicating a numerical measure of a diagnostic relevance between the received at least a medical test and a type of physiological state data;

wherein each remedial attribute list entry of the ranked remedial attribute list is ranked according to a respective remedial process significance score;

transmitting the ranked remedial attribute list to the at least a second computing device, said ranked remedial attribute list configured to display at least a portion of the plurality of remedial attribute list entries to the user on the at least a second computing device;

receiving a selection of a remedial attribute list entry displayed, using the graphical user interface, on the second computing device from the user by way of the graphical user interface; and modifying the ranked remedial attribute list based upon the selection of the remedial attribute list entry to produce a modified remedial attribute list, said modified remedial attribute list comprising a modified plurality of remedial attribute list entries;

generating a plurality of treatment schemas, wherein;

each treatment schema of the plurality of treatment schemas includes a treatment schema attribute listing having a plurality of treatment schema attribute listing entries;

the plurality of treatment schema attribute listing entries includes an attribute listing entry corresponding to each modified remedial attribute list entry of the modified plurality of remedial attribute list entries; and each treatment schema attribute listing entry indicates a degree of impact on a factor represented by a modified remedial attribute list entry of the modified plurality of remedial attribute list entries;

selecting a treatment schema from the plurality of treatment schemas, wherein selecting the treatment schema further comprises:

generating a loss function of the plurality of treatment schemas and the remedial attribute list;

minimizing the loss function; and selecting the treatment schema from the plurality of treatment schemas as a function of minimizing the loss function;

determining a second treatment schema which maximizes impact on life expectancy of the user by minimizing the loss function based on all treatment schema attribute listing entries except life expectancy impact set to zero; and transmitting the selected treatment schema and the second treatment schema to the at least a second computing device.

* * * * *